(12) United States Patent
Martin

(10) Patent No.: US 10,925,625 B2
(45) Date of Patent: *Feb. 23, 2021

(54) COMPLEX WIRE FORMED DEVICES

(71) Applicant: Covidien LP, Mansfield, MA (US)

(72) Inventor: Brian B. Martin, Felton, CA (US)

(73) Assignee: COVIDIEN LP, Mansfield, MA (US)

( * ) Notice: Subject to any disclaimer, the term of this patent is extended or adjusted under 35 U.S.C. 154(b) by 274 days.

This patent is subject to a terminal disclaimer.

(21) Appl. No.: 16/119,891

(22) Filed: Aug. 31, 2018

(65) Prior Publication Data

US 2019/0015121 A1    Jan. 17, 2019

Related U.S. Application Data

(63) Continuation of application No. 15/056,456, filed on Feb. 29, 2016, now Pat. No. 10,076,346, which is a continuation of application No. 13/946,901, filed on Jul. 19, 2013, now Pat. No. 9,271,747, which is a continuation of application No. 11/736,537, filed on Apr. 17, 2007, now Pat. No. 8,512,352.

(51) Int. Cl.
| | |
|---|---|
| A61B 17/221 | (2006.01) |
| A61B 17/3205 | (2006.01) |
| A61F 2/01 | (2006.01) |
| A61B 17/00 | (2006.01) |

(52) U.S. Cl.
CPC ...... *A61B 17/221* (2013.01); *A61B 17/32056* (2013.01); *A61B 2017/00867* (2013.01); *A61B 2017/2212* (2013.01); *A61B 2017/2215* (2013.01); *A61B 2017/2217* (2013.01); *A61F 2/013* (2013.01)

(58) Field of Classification Search
CPC ............ A61B 17/221; A61B 17/32056; A61B 2017/22081; A61B 2017/2212; A61B 2017/2215; A61B 2017/2217; A61F 2/013
See application file for complete search history.

(56) References Cited

U.S. PATENT DOCUMENTS

| | | |
|---|---|---|
| 1,054,960 A | 3/1913 | Butner |
| 2,918,919 A | 12/1959 | Wallace |
| 2,943,626 A | 7/1960 | Enrico |
| 3,108,593 A | 10/1963 | Glassman |
| 3,108,594 A | 10/1963 | Glassman |
| 3,996,938 A | 12/1976 | Clark |

(Continued)

FOREIGN PATENT DOCUMENTS

| | | |
|---|---|---|
| DE | 3501707 A1 | 7/1986 |
| EP | 1312314 A1 | 5/2003 |

(Continued)

OTHER PUBLICATIONS

Extended European Search Report dated Apr. 7, 2017; European Application No. 08807060.2.

*Primary Examiner* — Ryan J. Severson

(74) *Attorney, Agent, or Firm* — Fortem IP LLP; Mary Fox

(57) ABSTRACT

The devices and methods described herein relate to jointless construction of complex structures. Such devices have applicability in through-out the body, including clearing of blockages within body lumens, such as the vasculature, by addressing the frictional resistance on the obstruction prior to attempting to translate and/or mobilize the obstruction within the body lumen.

21 Claims, 12 Drawing Sheets

(56) References Cited

U.S. PATENT DOCUMENTS

| | | |
|---|---|---|
| 4,347,846 A | 9/1982 | Dormia |
| 4,611,594 A | 9/1986 | Grayhack et al. |
| 4,612,931 A | 9/1986 | Dormia |
| 4,633,871 A | 1/1987 | Shinozuka |
| 4,699,147 A | 10/1987 | Chilson et al. |
| 4,790,812 A | 12/1988 | Hawkins et al. |
| 4,807,626 A | 2/1989 | McGirr |
| 4,832,055 A | 5/1989 | Palestrant |
| 4,873,978 A | 10/1989 | Ginsburg |
| 4,969,891 A | 11/1990 | Gewertz |
| 5,057,114 A | 10/1991 | Wittich et al. |
| 5,059,178 A | 10/1991 | Ya |
| 5,098,441 A | 3/1992 | Wechler |
| 5,102,415 A | 4/1992 | Guenther et al. |
| 5,147,400 A | 9/1992 | Kaplan et al. |
| 5,152,777 A | 10/1992 | Goldberg et al. |
| 5,190,554 A | 3/1993 | Coddington et al. |
| 5,192,286 A | 3/1993 | Phan et al. |
| 5,300,086 A | 4/1994 | Gory et al. |
| 5,330,482 A | 7/1994 | Gibbs et al. |
| 5,397,320 A | 3/1995 | Essig et al. |
| 5,443,478 A | 8/1995 | Purdy |
| 5,458,375 A | 10/1995 | Anspach et al. |
| 5,496,330 A | 3/1996 | Bates et al. |
| 5,509,900 A | 4/1996 | Kirkman |
| 5,611,803 A | 3/1997 | Heaven et al. |
| 5,653,684 A | 8/1997 | Laptewicz et al. |
| 5,658,296 A | 8/1997 | Bates et al. |
| 5,709,704 A | 1/1998 | Nott et al. |
| 5,733,302 A | 3/1998 | Myler et al. |
| 5,741,325 A | 4/1998 | Chaikof et al. |
| 5,792,156 A | 8/1998 | Perouse |
| 5,827,324 A | 10/1998 | Cassell et al. |
| 5,846,251 A | 12/1998 | Hart |
| 5,895,398 A | 4/1999 | Wensel et al. |
| 5,947,995 A | 9/1999 | Samuels |
| 5,968,090 A | 10/1999 | Ratcliff et al. |
| 5,971,938 A | 10/1999 | Hart et al. |
| 5,972,019 A | 10/1999 | Engelson et al. |
| 5,989,266 A | 11/1999 | Foster |
| 6,001,118 A | 12/1999 | Daniel et al. |
| 6,033,394 A | 3/2000 | Vidlund et al. |
| 6,053,932 A | 4/2000 | Daniel et al. |
| 6,066,149 A | 5/2000 | Samson et al. |
| 6,066,158 A | 5/2000 | Engelson et al. |
| 6,096,053 A | 8/2000 | Bates |
| 6,099,534 A | 8/2000 | Bates et al. |
| 6,159,220 A | 12/2000 | Gobron et al. |
| 6,165,200 A | 12/2000 | Tsugita et al. |
| 6,168,579 B1 | 1/2001 | Tsugita |
| 6,168,603 B1 | 1/2001 | Leslie et al. |
| 6,174,318 B1 | 1/2001 | Bates et al. |
| 6,190,394 B1 | 2/2001 | Lind et al. |
| 6,217,609 B1 | 4/2001 | Haverkost |
| 6,221,006 B1 | 4/2001 | Dubrul et al. |
| 6,224,612 B1 | 5/2001 | Bates et al. |
| 6,245,089 B1 | 6/2001 | Daniel et al. |
| 6,248,113 B1 | 6/2001 | Fina |
| 6,264,664 B1 | 7/2001 | Avellanet |
| 6,299,612 B1 | 10/2001 | Ouchi |
| 6,302,895 B1 | 10/2001 | Gobron et al. |
| 6,309,399 B1 | 10/2001 | Barbut et al. |
| 6,325,807 B1 | 12/2001 | Que |
| 6,348,056 B1 | 2/2002 | Bates et al. |
| 6,350,266 B1 | 2/2002 | White et al. |
| 6,364,895 B1 | 4/2002 | Greenhalgh |
| 6,371,971 B1 | 4/2002 | Tsugita et al. |
| 6,383,195 B1 | 5/2002 | Richard |
| 6,383,196 B1 | 5/2002 | Leslie et al. |
| 6,402,761 B2 | 6/2002 | McAlister |
| 6,402,771 B1 | 6/2002 | Palmer et al. |
| 6,409,750 B1 | 6/2002 | Hyodoh et al. |
| 6,416,505 B1 | 7/2002 | Fleischman et al. |
| 6,425,909 B1 | 7/2002 | Dieck et al. |
| 6,436,112 B2 | 8/2002 | Wensel et al. |
| 6,443,972 B1 | 9/2002 | Bosma et al. |
| 6,458,139 B1 | 10/2002 | Palmer et al. |
| 6,485,497 B2 | 11/2002 | Wensel et al. |
| 6,494,884 B2 | 12/2002 | Gifford et al. |
| 6,506,204 B2 | 1/2003 | Mazzocchi |
| 6,514,273 B1 | 2/2003 | Voss et al. |
| 6,517,550 B1 | 2/2003 | Konya et al. |
| 6,530,935 B2 | 3/2003 | Wensel et al. |
| 6,537,297 B2 | 3/2003 | Tsugita et al. |
| 6,540,657 B2 | 4/2003 | Cross et al. |
| 6,544,279 B1 | 4/2003 | Hopkins et al. |
| 6,551,342 B1 | 4/2003 | Shen et al. |
| 6,575,997 B1 | 6/2003 | Palmer et al. |
| 6,585,753 B2 | 7/2003 | Eder et al. |
| 6,592,605 B2 | 7/2003 | Lenker et al. |
| 6,592,607 B1 | 7/2003 | Palmer et al. |
| 6,602,265 B2 | 8/2003 | Dubrul et al. |
| 6,602,271 B2 | 8/2003 | Adams et al. |
| 6,605,102 B1 | 8/2003 | Mazzocchi et al. |
| 6,610,077 B1 | 8/2003 | Hancock et al. |
| 6,616,679 B1 | 9/2003 | Khosravi et al. |
| 6,620,148 B1 | 9/2003 | Tsugita |
| 6,620,172 B1 | 9/2003 | Dretler et al. |
| 6,635,068 B1 | 10/2003 | Dubrul et al. |
| 6,636,758 B2 | 10/2003 | Sanchez et al. |
| 6,638,245 B2 | 10/2003 | Miller et al. |
| 6,641,590 B1 | 11/2003 | Palmer et al. |
| 6,645,199 B1 | 11/2003 | Jenkins et al. |
| 6,652,505 B1 | 11/2003 | Tsugita |
| 6,652,537 B2 | 11/2003 | Mercereau et al. |
| 6,652,548 B2 | 11/2003 | Evans et al. |
| 6,660,021 B1 | 12/2003 | Palmer et al. |
| 6,663,650 B2 | 12/2003 | Sepetka et al. |
| 6,673,042 B1 | 1/2004 | Samson et al. |
| 6,673,080 B2 | 1/2004 | Reynolds et al. |
| 6,679,893 B1 | 1/2004 | Tran |
| 6,685,738 B2 | 2/2004 | Chouinard et al. |
| 6,692,508 B2 | 2/2004 | Wensel et al. |
| 6,692,509 B2 | 2/2004 | Wensel et al. |
| 6,695,858 B1 | 2/2004 | Dubrul et al. |
| 6,702,782 B2 | 3/2004 | Miller et al. |
| 6,709,465 B2 | 3/2004 | Mitchell et al. |
| 6,712,835 B2 | 3/2004 | Mazzocchi et al. |
| 6,730,104 B1 | 5/2004 | Sepetka et al. |
| 6,740,096 B2 | 5/2004 | Teague et al. |
| 6,745,080 B2 | 6/2004 | Koblish |
| 6,746,468 B1 | 6/2004 | Sepetka et al. |
| 6,749,619 B2 | 6/2004 | Ouriel et al. |
| 6,755,813 B2 | 6/2004 | Ouriel et al. |
| 6,800,080 B1 | 10/2004 | Bates |
| 6,824,545 B2 | 11/2004 | Sepetka et al. |
| 6,840,950 B2 | 1/2005 | Stanford et al. |
| 6,872,211 B2 | 3/2005 | White et al. |
| 6,872,216 B2 | 3/2005 | Daniel et al. |
| 6,890,341 B2 | 5/2005 | Dieck et al. |
| 6,893,431 B2 | 5/2005 | Naimark et al. |
| 6,905,503 B2 | 6/2005 | Gifford et al. |
| 6,913,612 B2 | 7/2005 | Palmer et al. |
| 6,936,059 B2 | 8/2005 | Belef |
| 6,939,362 B2 | 9/2005 | Boyle et al. |
| 6,945,977 B2 | 9/2005 | Demarais et al. |
| 6,953,465 B2 | 10/2005 | Dieck et al. |
| 6,964,672 B2 | 11/2005 | Brady et al. |
| 7,004,955 B2 | 2/2006 | Shen et al. |
| 7,004,956 B2 | 2/2006 | Palmer et al. |
| 7,037,320 B2 | 5/2006 | Brady et al. |
| 7,058,456 B2 | 6/2006 | Pierce |
| 7,097,653 B2 | 8/2006 | Freudenthal et al. |
| 7,101,380 B2 | 9/2006 | Khachin et al. |
| 7,169,165 B2 | 1/2007 | Belef et al. |
| 7,179,273 B1 | 2/2007 | Palmer et al. |
| 7,182,771 B1 | 2/2007 | Houser et al. |
| 7,220,271 B2 | 5/2007 | Clubb et al. |
| 7,235,061 B2 | 6/2007 | Tsugita |
| 7,316,692 B2 | 1/2008 | Huffmaster |
| 7,534,252 B2 | 5/2009 | Sepetka et al. |
| 7,591,825 B2 | 9/2009 | Leslie et al. |
| 7,691,121 B2 | 4/2010 | Rosenbluth et al. |
| 7,731,722 B2 | 6/2010 | Lavelle et al. |

(56) References Cited

U.S. PATENT DOCUMENTS

| | | |
|---|---|---|
| 8,105,333 B2 | 1/2012 | Sepetka et al. |
| 8,142,445 B2 | 3/2012 | Teague |
| 8,157,811 B2 | 4/2012 | Shinozuka et al. |
| 8,211,115 B2 | 7/2012 | Cheng et al. |
| 8,267,940 B2 | 9/2012 | Sepetka et al. |
| 8,512,352 B2 | 8/2013 | Martin |
| 8,535,334 B2 | 9/2013 | Martin |
| 8,545,526 B2 | 10/2013 | Martin et al. |
| 8,603,014 B2 | 12/2013 | Alleman et al. |
| 8,801,748 B2 | 8/2014 | Martin |
| 8,837,800 B1 | 9/2014 | Bammer et al. |
| 9,119,656 B2 | 9/2015 | Bose et al. |
| 9,126,018 B1 | 9/2015 | Garrison |
| 9,211,132 B2 | 12/2015 | Bowman |
| 9,241,699 B1 | 1/2016 | Kume et al. |
| 9,254,371 B2 | 2/2016 | Martin et al. |
| 9,265,512 B2 | 2/2016 | Garrison et al. |
| 9,271,747 B2 | 3/2016 | Martin |
| 9,271,748 B2 | 3/2016 | Martin |
| 9,308,007 B2 | 4/2016 | Cully et al. |
| 9,399,118 B2 | 7/2016 | Kume et al. |
| 9,445,828 B2 | 9/2016 | Turjman et al. |
| 9,445,829 B2 | 9/2016 | Brady et al. |
| 9,492,637 B2 | 11/2016 | Garrison et al. |
| 9,539,022 B2 | 1/2017 | Bowman |
| 9,561,345 B2 | 2/2017 | Garrison et al. |
| 9,579,119 B2 | 2/2017 | Cully et al. |
| 9,585,741 B2 | 3/2017 | Ma |
| 9,642,635 B2 | 5/2017 | Vale et al. |
| 9,655,633 B2 | 5/2017 | Leynov et al. |
| 9,717,514 B2 | 8/2017 | Martin et al. |
| 9,737,318 B2 | 8/2017 | Monstadt et al. |
| 9,770,251 B2 | 9/2017 | Bowman et al. |
| 9,801,643 B2 | 10/2017 | Hansen et al. |
| 9,861,783 B2 | 1/2018 | Garrison et al. |
| 9,993,257 B2 | 6/2018 | Losordo et al. |
| 10,028,782 B2 | 7/2018 | Orion |
| 10,029,008 B2 | 7/2018 | Creighton |
| 10,039,906 B2 | 8/2018 | Kume et al. |
| 10,076,346 B2 * | 9/2018 | Martin ............ A61B 17/221 |
| 2001/0031971 A1 | 10/2001 | Dretler et al. |
| 2001/0041909 A1 | 11/2001 | Tsugita et al. |
| 2001/0044634 A1 | 11/2001 | Don et al. |
| 2001/0051810 A1 | 12/2001 | Dubrul et al. |
| 2002/0002396 A1 | 1/2002 | Fulkerson |
| 2002/0004667 A1 | 1/2002 | Adams et al. |
| 2002/0026211 A1 | 2/2002 | Khosravi et al. |
| 2002/0058904 A1 | 5/2002 | Boock et al. |
| 2002/0062135 A1 | 5/2002 | Mazzocchi et al. |
| 2002/0072764 A1 | 6/2002 | Sepetka et al. |
| 2002/0082558 A1 | 6/2002 | Samson et al. |
| 2002/0123765 A1 | 9/2002 | Sepetka et al. |
| 2002/0151928 A1 | 10/2002 | Leslie et al. |
| 2002/0169474 A1 | 11/2002 | Kusleika et al. |
| 2002/0188314 A1 | 12/2002 | Anderson et al. |
| 2002/0193825 A1 | 12/2002 | McGuckin et al. |
| 2003/0004542 A1 | 1/2003 | Wensel et al. |
| 2003/0023265 A1 | 1/2003 | Forber |
| 2003/0040771 A1 | 2/2003 | Hyodoh et al. |
| 2003/0050663 A1 | 3/2003 | Khachin et al. |
| 2003/0060782 A1 | 3/2003 | Bose et al. |
| 2003/0093087 A1 | 5/2003 | Jones et al. |
| 2003/0139750 A1 | 7/2003 | Shinozuka et al. |
| 2003/0144687 A1 | 7/2003 | Brady et al. |
| 2003/0153935 A1 | 8/2003 | Mialhe |
| 2003/0191492 A1 | 10/2003 | Gellman et al. |
| 2003/0195556 A1 | 10/2003 | Stack et al. |
| 2004/0068288 A1 | 4/2004 | Palmer et al. |
| 2004/0073243 A1 | 4/2004 | Sepetka et al. |
| 2004/0079429 A1 | 4/2004 | Miller et al. |
| 2004/0116941 A1 | 6/2004 | Reynolds et al. |
| 2004/0122445 A1 | 6/2004 | Butler et al. |
| 2004/0133232 A1 | 7/2004 | Rosenbluth et al. |
| 2004/0138692 A1 | 7/2004 | Phung et al. |
| 2004/0153025 A1 | 8/2004 | Seifert et al. |
| 2004/0153118 A1 | 8/2004 | Clubb et al. |
| 2004/0172056 A1 | 9/2004 | Guterman et al. |
| 2004/0199201 A1 | 10/2004 | Kellett et al. |
| 2004/0199243 A1 | 10/2004 | Yodfat |
| 2004/0210116 A1 | 10/2004 | Nakao |
| 2004/0267301 A1 | 12/2004 | Boylan et al. |
| 2005/0004594 A1 | 1/2005 | Nool et al. |
| 2005/0033348 A1 | 2/2005 | Sepetka et al. |
| 2005/0038447 A1 | 2/2005 | Huffmaster |
| 2005/0043680 A1 | 2/2005 | Segal et al. |
| 2005/0043756 A1 | 2/2005 | Lavelle et al. |
| 2005/0049619 A1 | 3/2005 | Sepetka et al. |
| 2005/0055033 A1 | 3/2005 | Leslie et al. |
| 2005/0055047 A1 | 3/2005 | Greenhalgh |
| 2005/0059995 A1 | 3/2005 | Sepetka et al. |
| 2005/0075648 A1 | 4/2005 | Komiya |
| 2005/0080356 A1 | 4/2005 | Dapolito et al. |
| 2005/0085826 A1 | 4/2005 | Nair et al. |
| 2005/0085847 A1 | 4/2005 | Galdonik et al. |
| 2005/0085849 A1 | 4/2005 | Sepetka et al. |
| 2005/0090857 A1 | 4/2005 | Kusleika et al. |
| 2005/0090858 A1 | 4/2005 | Pavlovic |
| 2005/0096668 A1 | 5/2005 | McAlister |
| 2005/0125024 A1 | 6/2005 | Sepetka et al. |
| 2005/0131450 A1 | 6/2005 | Nicholson et al. |
| 2005/0171566 A1 | 8/2005 | Kanamaru |
| 2005/0203571 A1 | 9/2005 | Mazzocchi et al. |
| 2005/0209609 A1 | 9/2005 | Wallace |
| 2005/0216030 A1 | 9/2005 | Sepetka et al. |
| 2005/0216050 A1 | 9/2005 | Sepetka et al. |
| 2005/0234501 A1 | 10/2005 | Barone |
| 2005/0234505 A1 | 10/2005 | Diaz et al. |
| 2005/0251151 A1 | 11/2005 | Teague |
| 2005/0261706 A1 | 11/2005 | Cheng et al. |
| 2005/0267491 A1 | 12/2005 | Kellett et al. |
| 2005/0277978 A1 | 12/2005 | Greenhalgh |
| 2005/0283166 A1 | 12/2005 | Greenhalgh |
| 2005/0283186 A1 | 12/2005 | Berrada et al. |
| 2006/0004404 A1 | 1/2006 | Khachin et al. |
| 2006/0009784 A1 | 1/2006 | Behl et al. |
| 2006/0047286 A1 | 3/2006 | West |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0095070 A1 | 5/2006 | Gilson et al. |
| 2006/0129166 A1 | 6/2006 | Lavelle |
| 2006/0129180 A1 | 6/2006 | Tsugita et al. |
| 2006/0155305 A1 | 7/2006 | Freudenthal et al. |
| 2006/0190070 A1 | 8/2006 | Dieck et al. |
| 2006/0195137 A1 | 8/2006 | Sepetka et al. |
| 2006/0229638 A1 | 10/2006 | Abrams et al. |
| 2006/0253145 A1 | 11/2006 | Lucas |
| 2006/0276805 A1 | 12/2006 | Yu |
| 2006/0282111 A1 | 12/2006 | Morsi |
| 2006/0293697 A1 | 12/2006 | Nakao et al. |
| 2007/0112374 A1 | 5/2007 | Paul et al. |
| 2007/0118165 A1 | 5/2007 | Demello et al. |
| 2007/0185500 A1 | 8/2007 | Martin et al. |
| 2007/0185501 A1 | 8/2007 | Martin et al. |
| 2007/0197103 A1 | 8/2007 | Martin et al. |
| 2007/0198029 A1 | 8/2007 | Martin et al. |
| 2007/0198030 A1 | 8/2007 | Martin et al. |
| 2007/0208367 A1 | 9/2007 | Fiorella et al. |
| 2007/0225749 A1 | 9/2007 | Martin et al. |
| 2007/0265656 A1 | 11/2007 | Amplatz et al. |
| 2008/0109031 A1 | 5/2008 | Sepetka et al. |
| 2008/0183198 A1 | 7/2008 | Sepetka et al. |
| 2008/0188885 A1 | 8/2008 | Sepetka et al. |
| 2008/0262528 A1 | 10/2008 | Martin |
| 2008/0262532 A1 | 10/2008 | Martin |
| 2009/0069828 A1 | 3/2009 | Martin et al. |
| 2009/0192518 A1 | 7/2009 | Leanna et al. |
| 2009/0287291 A1 | 11/2009 | Becking et al. |
| 2009/0299393 A1 | 12/2009 | Martin et al. |
| 2010/0076452 A1 | 3/2010 | Sepetka et al. |
| 2010/0185210 A1 | 7/2010 | Hauser et al. |
| 2011/0166586 A1 | 7/2011 | Sepetka et al. |
| 2011/0288572 A1 | 11/2011 | Martin |
| 2012/0143230 A1 | 6/2012 | Sepetka et al. |

(56) References Cited

U.S. PATENT DOCUMENTS

| | | |
|---|---|---|
| 2012/0197285 A1 | 8/2012 | Martin et al. |
| 2013/0030461 A1 | 1/2013 | Marks et al. |
| 2013/0281788 A1 | 10/2013 | Garrison |
| 2014/0005717 A1 | 1/2014 | Martin et al. |
| 2014/0031856 A1 | 1/2014 | Martin |
| 2014/0148841 A1 | 5/2014 | Martin |
| 2014/0276074 A1 | 9/2014 | Warner |
| 2014/0343595 A1 | 11/2014 | Monstadt et al. |
| 2015/0359547 A1 | 12/2015 | Vale et al. |
| 2016/0015402 A1 | 1/2016 | Brady et al. |
| 2016/0015935 A1 | 1/2016 | Chan et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113665 A1 | 4/2016 | Brady et al. |
| 2016/0151618 A1 | 6/2016 | Powers et al. |
| 2016/0157985 A1 | 6/2016 | Vo et al. |
| 2016/0174996 A1* | 6/2016 | Martin .................. A61B 17/221 606/127 |
| 2016/0199620 A1 | 7/2016 | Pokorney et al. |
| 2016/0296690 A1 | 10/2016 | Kume et al. |
| 2016/0302808 A1 | 10/2016 | Loganathan et al. |
| 2016/0375180 A1 | 12/2016 | Anzai |
| 2017/0079766 A1 | 3/2017 | Wang et al. |
| 2017/0079767 A1 | 3/2017 | Leon-Yip |
| 2017/0086862 A1 | 3/2017 | Vale |
| 2017/0100143 A1 | 4/2017 | Grandfield |
| 2017/0105743 A1 | 4/2017 | Vale et al. |
| 2017/0164963 A1 | 6/2017 | Goyal |
| 2017/0215902 A1 | 8/2017 | Leynov et al. |
| 2017/0224953 A1 | 8/2017 | Tran et al. |
| 2017/0281909 A1 | 10/2017 | Northrop et al. |
| 2017/0290599 A1 | 10/2017 | Youn et al. |
| 2018/0049762 A1 | 2/2018 | Seip et al. |
| 2018/0084982 A1 | 3/2018 | Yamashita et al. |
| 2018/0116717 A1 | 5/2018 | Taff et al. |
| 2018/0132876 A1 | 5/2018 | Zaidat |
| 2018/0140314 A1 | 5/2018 | Goyal et al. |
| 2018/0140315 A1 | 5/2018 | Bowman et al. |
| 2018/0140354 A1 | 5/2018 | Lam et al. |
| 2018/0185614 A1 | 7/2018 | Garrison et al. |
| 2019/0015121 A1* | 1/2019 | Martin ............. A61B 17/32056 |

FOREIGN PATENT DOCUMENTS

| | | |
|---|---|---|
| EP | 2319575 B1 | 11/2013 |
| JP | 2002537943 A | 11/2002 |
| JP | 2008539958 A | 11/2008 |
| JP | 2014004219 A | 1/2014 |
| JP | 2018118132 A | 8/2018 |
| KR | 20180102877 A | 9/2018 |
| WO | 9409845 A1 | 5/1994 |
| WO | 9509586 A1 | 4/1995 |
| WO | 9601591 A1 | 1/1996 |
| WO | 9617634 A2 | 6/1996 |
| WO | 9619941 A1 | 7/1996 |
| WO | 9727808 A1 | 8/1997 |
| WO | 9727893 A1 | 8/1997 |
| WO | 9803120 A1 | 1/1998 |
| WO | 0053120 A1 | 9/2000 |
| WO | 0072909 A1 | 12/2000 |
| WO | 0132254 A1 | 5/2001 |
| WO | 0154622 A1 | 8/2001 |
| WO | 0167967 A1 | 9/2001 |
| WO | 0202162 A2 | 1/2002 |
| WO | 0228291 A2 | 4/2002 |
| WO | 03000334 A1 | 1/2003 |
| WO | 03061730 A2 | 7/2003 |
| WO | 03089039 A1 | 10/2003 |
| WO | 2006031410 A2 | 3/2006 |
| WO | 2006122076 A1 | 11/2006 |
| WO | 2007092820 A2 | 8/2007 |
| WO | 2008036156 A1 | 3/2008 |
| WO | 2008131116 A1 | 10/2008 |
| WO | 2009034456 A2 | 3/2009 |
| WO | 2009086482 A1 | 7/2009 |
| WO | 2011091383 A1 | 7/2011 |
| WO | 2012009675 A2 | 1/2012 |
| WO | 2012162437 A1 | 11/2012 |
| WO | 2015141317 A1 | 9/2015 |
| WO | 2017192999 A1 | 11/2017 |
| WO | 2018019829 A1 | 2/2018 |
| WO | 2018033401 A1 | 2/2018 |
| WO | 2018046408 A2 | 3/2018 |
| WO | 2018137029 A1 | 8/2018 |
| WO | 2018137030 A1 | 8/2018 |
| WO | 2018145212 A1 | 8/2018 |
| WO | 2018156813 A1 | 8/2018 |
| WO | 2018172891 A1 | 9/2018 |
| WO | 2018187776 A1 | 10/2018 |

\* cited by examiner

COMPLEX WIRE FORMED DEVICES

CROSS-REFERENCE TO RELATED APPLICATIONS

This application is a continuation of U.S. patent application Ser. No. 15/056,456, filed on Feb. 29, 2016, which is a continuation of U.S. patent application Ser. No. 13/946,901, filed on Jul. 19, 2013, now U.S. Pat. No. 9,271,747, which is a continuation of U.S. patent application Ser. No. 11/736,537, filed on Apr. 17, 2007, now U.S. Pat. No. 8,512,352, all of which are incorporated herein by reference in their entirety.

FIELD OF THE INVENTION

The devices described herein are constructed in wire form where the wires diverge from a main bundle to form a variety of shapes that form a composite device. The benefit of such a diverging wire construction is that the composite complex device can be of a "joint-less" construction. Such devices have applicability in through-out the body, including clearing of blockages within body lumens, such as the vasculature, by addressing the frictional resistance on the obstruction prior to attempting to translate and/or mobilize the obstruction within the body lumen.

BACKGROUND OF THE INVENTION

Many medical device applications require advancement of device in a reduced profile to a remote site within the body, where on reaching a target site, the device assumes or is deployed into a relatively larger profile. Applications in the cerebral vasculature are one such example of medical procedures where a catheter advances from a remote part of the body (typically a leg) through the vasculature and into the cerebral region of the vasculature to deploy a device. Accordingly, the deployed devices must be capable of achieving a larger profile while being able to fit within a small catheter or microcatheter. In addition, the degree to which a physician is limited in accessing remote regions of the cerebral vasculature is directly related to the limited ability of the device to constrain into a reduced profile for delivery.

Treatment of ischemic stroke is one such area where a need remains to deliver a device in a reduced profile and deploy the device to ultimately remove a blockage in an artery leading to the brain. Left untreated, the blockage causes a lack of supply of oxygen and nutrients to the brain tissue. The brain relies on its arteries to supply oxygenated blood from the heart and lungs. The blood returning from the brain carries carbon dioxide and cellular waste. Blockages that interfere with this supply eventually cause the brain tissue to stop functioning. If the disruption in supply occurs for a sufficient amount of time, the continued lack of nutrients and oxygen causes irreversible cell death (infarction). Accordingly, immediate medical treatment of an ischemic stroke is critical for the recovery of a patient.

Naturally, areas outside of ischemic stroke applications can also benefit from devices that can assume a profile for ultimate delivery to remote regions of the body.

Regardless of the area where the device is to be used, when fabricating such a device the joints between adjacent shapes or sections of the device often impede the ability of the device to assume a sufficiently reduced profile or interfere with the geometry/stiffness of the device causing problems when navigating the device through the body. Also, joints lead to potential failure locations, and may lead to fractured and embolized components within the body. Such joints may include welded, glued, or otherwise separately joined pieces into one or more points of connection.

Accordingly, a need remains for devices that can assume deployed configurations and are fabricated to eliminate or reduce the number of joints and/or connection points in the device. Doing so allows the device to have a compact and smooth configuration making it easier for delivery through a microcatheter, and leads to a safer device less prone to breaking or embolizing.

SUMMARY OF THE INVENTION

The examples discussed herein show the inventive device in a form that is suitable to retrieve obstructions or clots within the vasculature. The term obstructions may include blood clot, plaque, cholesterol, thrombus, naturally occurring foreign bodies (i.e., a part of the body that is lodged within the lumen), a non-naturally occurring foreign body (i.e., a portion of a medical device or other non-naturally occurring substance lodged within the lumen.) However, the devices are not limited to such applications and can apply to any number of medical applications where elimination or reduction of the number of connection points is desired.

In one variation of the devices described herein, the device comprises a main bundle or group of wires that diverge to form a device having various shapes but few or no connections points or joints (where fabrication of such a construction is referred to as "jointless").

The term shape (or shaped section), when applied to the various shapes of the device, is intended to identify different parts of the device where the wires/fibers form different sections or portions of the device. Each such region or shape has a structure that serves a different function of the device. In one example of such a device, a first shape can be a connector portion and a second shape can be a basket or mesh shape. In this case, the first shape (the connector portion) has a different structure and serves a different function than the second shape (the basket or mesh shape). In another example, a first shape can be a connector portion, a second shape can be a traversing section, and the third shape can be a second connector shape. Again, each shape serves a different function (although in this example the first and third shapes may have similar structures). In most variations of the device, adjacent shapes will have different structures or will be separated by the wires that diverge/converge to form adjacent shapes (e.g., two adjacent shapes, each forming connector shapes but are separated by wires that traverse between the connector shapes). The different shapes may not necessarily be spaced axially along the device; instead, as shown below, two shapes may form a single connector portion (e.g., see FIG. 6C).

In one variation, the device is adapted for delivery through a catheter and includes a main bundle comprising a group of wires having a first end extending through the catheter and a second end, where the main bundle of wires diverge at the second end to form a first shaped section, the first shaped section further comprises an expanded profile and a reduced profile for delivery through the catheter, a plurality of individual subsets of wires each diverging from the first shaped section to form a second shaped section, and where the individual subsets of wires converge to form a third shaped section, where the third shaped section comprises an expanded profile and a reduced profile for delivery through the catheter, and where the convergence and divergence of wires occurs without junctions between wires.

The term diverge includes uncoupling or separating of joined wires. In addition, a group of wires that form a first shape may all diverge to form a new composite shape. For example, a bundle of wires may form a loop shape and ultimately bend to extend in a direction substantially normal to the loop shape. In such a case, the wires can be considered to diverge from the loop shape to form a second shape.

The devices of the present invention typically include a main bundle from which the wires extend. In most case, the main bundle extends for a length sufficient to withdraw the device from a body of a patient. Accordingly, in such cases, the main bundle shall extend through the length of a catheter. In alternate constructions, the main bundle may be affixed to a single wire or member. In such cases, the single wire or member is used to manipulate the device, which allows shortening of the length of the main bundle.

Devices of the present invention can incorporate any number of wires of different characteristics including, but not limited to, materials, shapes, sizes and/or diameters. Clearly, the number of permutations of device configurations is significant. Providing devices with such a composite construction allows for the manipulation of the device's properties to suite the intended application.

In an additional variation, the devices can also include a basket or mesh shape structure that assists in the removal of obstructions from the body. In some cases, these basket structures are used as a capturing section. Although any number of shapes is contemplated, a few examples of such shapes include a basket, a filter, a bag, a coil, a helical wire structure, a mesh, a single wound wire, and a plurality of crossing wires.

In some cases where the device is intended to remove obstructions from the vasculature, the device and catheter may be constructed to permit relative rotation of the ends of the device such that upon rotation a portion of the device converts to a high friction surface to aid in removing the obstruction.

As noted herein, the joint-less construction improves the flexibility and strength of the device by eliminating joints, connection points, or other attachment points. In addition, the joint-less construction improves the ability of the device to be delivered through a small microcatheter. As a result, the device and microcatheter are able to access remote regions of the vasculature.

The devices may be fabricated to be self-expanding upon deployment from a catheter. Alternatively, the devices can be constructed from shape-memory alloys such that they automatically deploy upon reaching a pre-determined transition temperature.

When used in the vasculature to retrieve obstructions, the devices may include a low friction mode (such as a set of parallel wires, or wires extending axially along the lumen or vessel) that converts to an increased friction mode (such as a compressed set of wires acting on the obstruction or a twisted set of wires acting on the obstruction). The increase in friction is an increase in the friction between the obstruction and the device (as opposed to the vessel wall. In some cases, the low friction mode is a low surface area mode and the high friction mode is a high surface area mode. When configured in the low friction mode, the device is better suited to engage the obstruction without the undesirable effect of prematurely mobilizing the obstruction or compacting the obstruction (e.g., when wires are slid across the obstruction in a transverse motion). Upon engaging the obstruction, the device will conform to a high friction mode with respect to the obstruction (in some cases the device will have an increased surface area mode). This high friction mode permits the device to better grip the obstruction for ultimate removal of the obstruction.

The operation of the devices and method described herein secure the obstruction, overcome the elastic forces of the obstruction, and then remove the obstruction from the anatomy without losing or fractionating the obstruction. In one variation of the invention, this is accomplished by the obstruction removal device interacting with the obstruction in the following manner: (1) a portion of the wires are delivered distal to the obstruction by passing either through the obstruction or between the obstruction and the vascular wall; (2) the traversing wires are pulled proximally to engage a basket shaped section of the device around the obstruction, the basket shaped section engages the obstruction without causing significant mobilization of the obstruction; (3) the device is pulled further proximally and the surrounding portion now mobilizes the obstruction.

As shown below, variations of the devices have a configuration that provides a path for a portion of the device to surround the obstruction. The paths are made using sets or subsets of wires that allow for low frictional translation of the device over the obstruction without causing axial translation of the obstruction. This mechanism is described in more detail below.

Once in the proper position, a portion of the device increases the frictional contact with the obstruction to disperse the pulling force more evenly across the obstruction. The increase points of contact allow for removal of the obstruction through tortuous anatomy while ensuring that the obstruction will not escape the encapsulation.

It should be noted that reference to surrounding, capturing or securing the obstruction includes partially and/or fully surrounding, engulfing, encapsulating, and/or securing the obstruction. In any case, a portion of the device engages the obstruction prior to translation of the obstruction within the lumen. As noted herein, a portion of the device may convert into a surrounding section (e.g., when wires reorient to increase the friction acting on the obstruction). Accordingly, these wires convert into a surrounding section.

It should be noted that in some variations of the invention, all or some of the device can be designed to increase their ability to adhere to the obstruction. For example, the wires may be coupled to an energy source (e.g., RF, ultrasonic, or thermal energy) to "weld" to the obstruction. Application of energy to the device can allow the surrounding portion to deform into the obstruction and "embed" within the obstruction. Alternatively, the device can impart a positive charge to the obstruction to partially liquefy the obstruction sufficiently to allow for easier removal. In another variation, a negative charge could be applied to further build thrombus and nest the device for better pulling force. The wires can be made stickier by use of a hydrophilic substance(s), or by chemicals that would generate a chemical bond to the surface of the obstruction. Alternatively, the filaments may reduce the temperature of the obstruction to congeal or adhere to the obstruction.

Additional devices and methods for treating ischemic stroke are discussed in commonly assigned U.S. patent application Ser. No. 11/671,450 filed Feb. 5, 2007; Ser. No. 11/684,521 filed Mar. 9, 2007; Ser. No. 11/684,535 filed Mar. 9, 2007; Ser. No. 11/684,541 filed Mar. 9, 2007; Ser. No. 11/684,546 filed Mar. 9, 2007; and Ser. No. 111/684,982 filed Mar. 12, 2007; the entirety of each of which is incorporated by reference. The principles of the invention as discussed herein may be applied to the above referenced cases to produce devices useful in treating ischemic stroke. In other words, the wire-shaped construction of devices according to present invention may assume the shapes disclosed in the above-referenced cases.

BRIEF DESCRIPTION OF THE DRAWINGS

Each of the following figures diagrammatically illustrates aspects of the invention. Variation of the invention from the aspects shown in the figures is contemplated.

DETAILED DESCRIPTION

It is understood that the examples below discuss uses in the cerebral vasculature (namely the arteries). However, unless specifically noted, variations of the device and method are not limited to use in the cerebral vasculature. Instead, the invention may have applicability in various parts of the body. Moreover, the invention may be used in various procedures where the benefits of the method and/or device are desired.

Figure 1A:
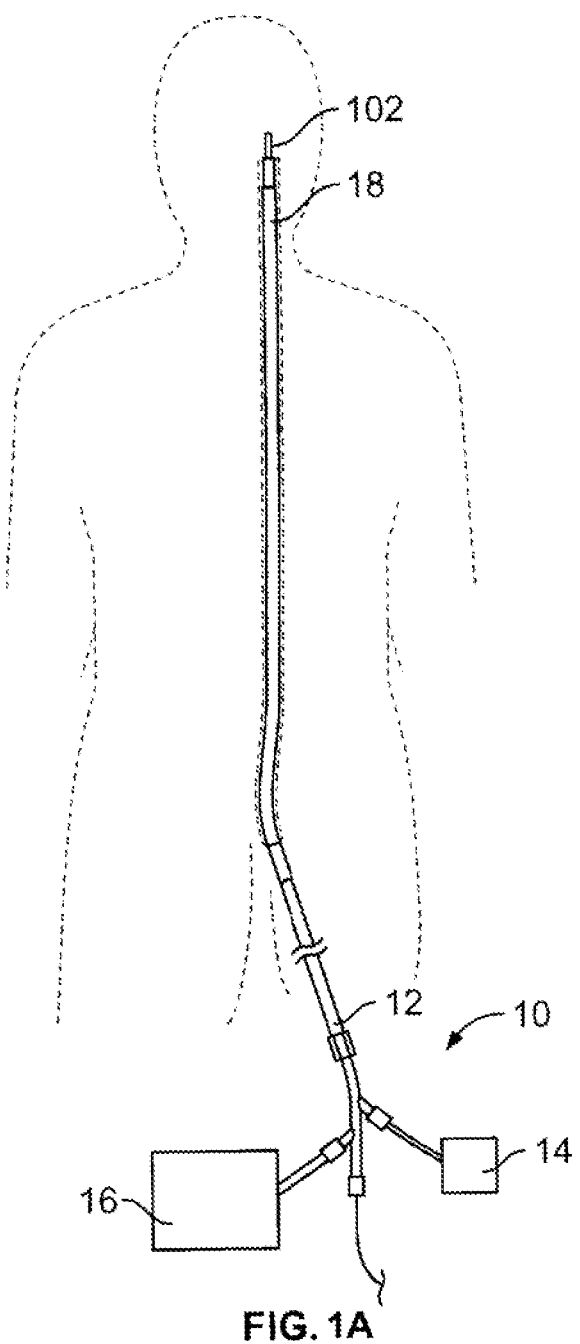
FIG. 1A illustrates an example of a device according to the present invention when used in a system for removing obstructions from body lumens.

FIG. 1A illustrates a system 10 for removing obstructions from body lumens as described herein. In the illustrated example, this variation of the system 10 is suited for removal of an obstruction in the cerebral vasculature. Typically, the system 10 includes a catheter 12 microcatheter, sheath, guide-catheter, or simple tube/sheath configuration for delivery of the obstruction removal device to the target anatomy. The catheter should be sufficient to deliver the device as discussed below. The catheter 12 may optionally include an inflatable balloon 18 for temporarily blocking blood flow or for expanding the vessel to release the obstruction.

It is noted that any number of catheters or microcatheters maybe used to locate the catheter/microcatheter 12 carrying the obstruction removal device (not illustrated) at the desired target site. Such techniques are well understood standard interventional catheterization techniques. Furthermore, the catheter 12 may be coupled to auxiliary or support components 14, 16 (e.g., energy controllers, power supplies, actuators for movement of the device(s), vacuum sources, inflation sources, sources for therapeutic substances, pressure monitoring, flow monitoring, various bio-chemical sensors, bio-chemical substance, etc.) Again, such components are within the scope of the system 10 described herein.

In addition, devices of the present invention may be packaged in kits including the components discussed above along with guiding catheters, various devices that assist in the stabilization or removal of the obstruction (e.g., proximal-assist devices that holds the proximal end of the obstruction in place preventing it from straying during removal or assisting in the removal of the obstruction), balloon-tipped guide catheters, dilators, etc.

Figure 1B:
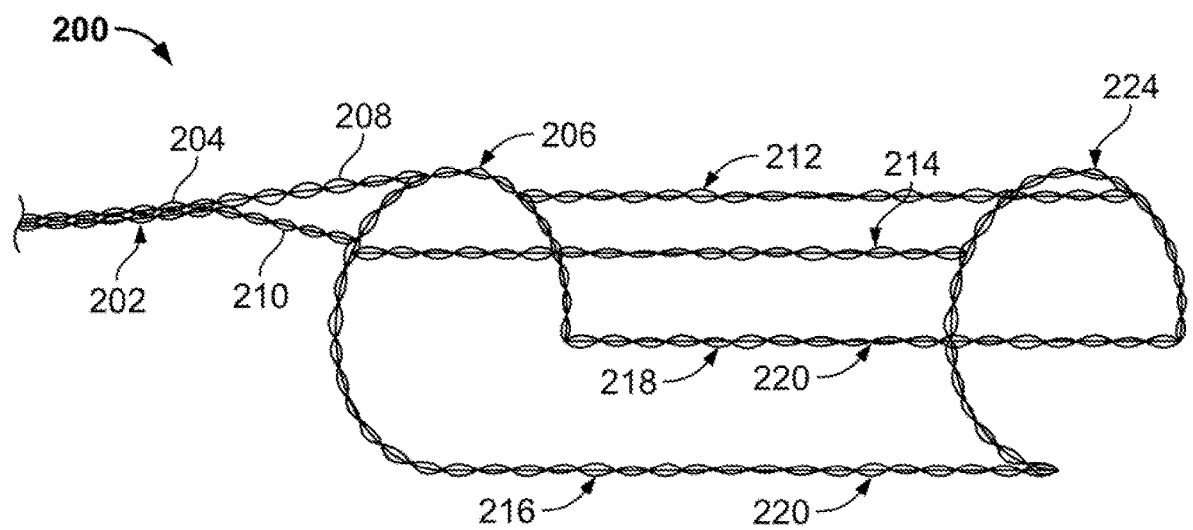
FIG. 1B illustrates a first variation of the device having a joint-less construction.

FIG. 1B illustrates a first variation of a device according to the features described herein. As shown, the device 200 generally includes a main bundle 202 comprising a group of individual wires 204. The individual wires 204 may be comprised of a number of different wires, or a single type of wire. Variations of the wires 204 are discussed in detail below; however, the wires 204 can be strands, filaments, or any similar structure that is able to be joined to form the device. The bundle 106 may be braided, wrapped, twisted, or joined in any manner such that they do not separate or become unbundled except where desired. As shown, the main bundle 202 diverges to form a first shaped section 206. In this particular example, the bundle 202 diverges in two sections 208, 210 which then diverge again to form the first shape 206.

Next, the wires 204 forming the first shape 206 diverge in groups or subsets of wires 212, 214, 216, 218, to form a second shaped section 220. Ultimately, the subsets of wires 212, 214, 216, 218 converge to form a third shaped section 224. The ends of the wires 204 may terminate in the final shape of the device. In other variations, the device is constructed such that the shapes formed by the divergence and convergence of the wires are formed by the center of the individual wires where all the ends of the wires are located in the main bundle 202. In such a configuration, the device will not contain any terminating ends. In such a case, the wires forming the shapes are continuous and the device is completely joint or connection free.

In the illustrated variation, the first shaped section and third shaped section 206, 224 form loop shapes while the second shaped section forms a series of traversing elements that extend between the loops. When formed into traversing elements, the wires extend substantially parallel to one another and normal to the shaped sections so that they can span between the first and third shaped sections.

As noted below, any number of shapes may be formed with this joint-less construction. In addition, the devices described herein may have any number of shaped sections. For example, in the illustrated variation, the first and second 206, 224 shaped sections form two loop type structures. However, the device may be constructed such that the wires diverge to form any number of looped shaped structures.

In any case, the individual wires 204 form a composite device 200 having individual sections that can serve various functions upon deployment of the device 200. The divergence and convergence of the wires minimizes the numbers of joints or connections that would otherwise be required to form the composite shape. Such a configuration produces a smooth geometry given that the wires forming the device 200 are continuous.

Figure 1C:
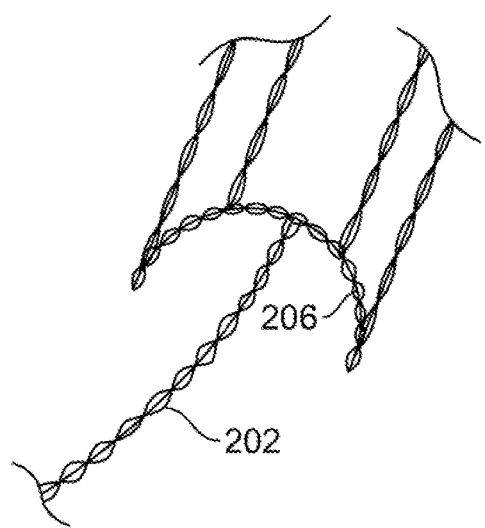
FIG. 1C illustrates another variation of a main bundle of wires diverging in a joint-less construction.

FIG. 1C illustrates a partial view of another variation of a device 200 according to the present invention. In this variation, the device 200 comprises a main bundle 202 where the main bundle 202 diverges to form the first shape 206. In contrast with the device shown in FIG. 1B, the main bundle 206 does not diverge to form sections 208, 210 prior to forming the first shape 206.

It is noted that any number of shapes, configurations, as well as any number of joined wires may be contemplated to form devices under the present disclosure. However, variations of the invention include selecting a number of wires 204 to produce specific structural properties to the device. For example, if it is desired that each subset 212, 214, 216, 218, have at least two wires, then naturally the first section, third section, and main bundle 202 must have at least two wires. However, in some cases, it may be desired that these sections have additional wires to impart the required characteristics. For example, in the illustrated variation, the main bundle may comprise any number of wires that do not diverge to form subsequent shapes in the device. In other words, not all of the wires forming a section are required to diverge to form an adjacent section. Instead, these non-diverging wires may simply "loop" back away from the device. In an additional variation, one or more wires may diverge to form a first shape and part of a second shape. Then the wires can loop back to converge again with the main bundle.

Of course, the opposite construction is also within the scope of this disclosure. Namely, that each wire from the main bundle diverges to form an adjacent section or shape.

FIGS. 2A to 2F show one example of the deployment of a basic structure of a device according to the present invention about an obstruction in a vessel. The figures are intended to demonstrate the initial placement of the device immediately prior to removal of the obstruction either using a filter or by torquing, rotating and/or twisting the device ends relative to one another. This action converts the device from a low friction device to a high friction device (where the low/high friction is the friction between the device and the obstruction). This action may also be referred to as a low surface area mode converting to a high surface area mode (in cases where the device extends beyond the obstruction and relative motion between ends of the device causes the device to shrink in axial length as it is twisted.)

Figure 2A:
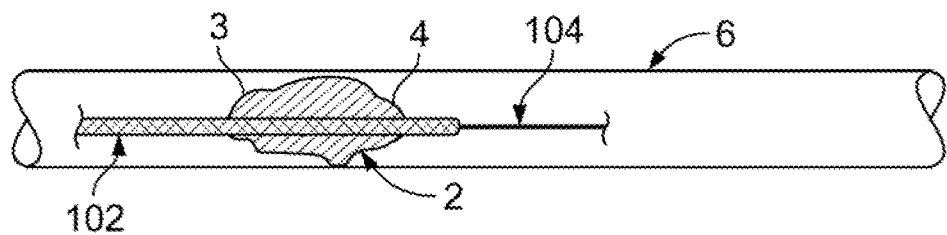
FIG. 2A illustrates an example of an obstruction lodged within a body lumen.

FIG. 2A illustrates an example of an obstruction 2 lodged within a body lumen or vessel 6. In the case where the vessel is a cerebral artery, the obstruction may result in an ischemic stroke. Using standard interventional catheterization techniques, a microcatheter 102 and guidewire 104 traverse the obstruction. The microcatheter 102 may be advanced through the obstruction 2. Alternatively, the microcatheter 102 may "push" aside the obstruction and is advanced around the obstruction. In any case, the microcatheter 102 travels from the near end 3 (or proximal side) of the obstruction 2 to the far end 4 (or distal side) of the obstruction 2. It is noted that the catheter 102 may be centered or off-center with respect to the obstruction 2. Furthermore, the device may or may not be used with a guidewire to navigate to the site and traverse the obstruction.

Figure 2B:
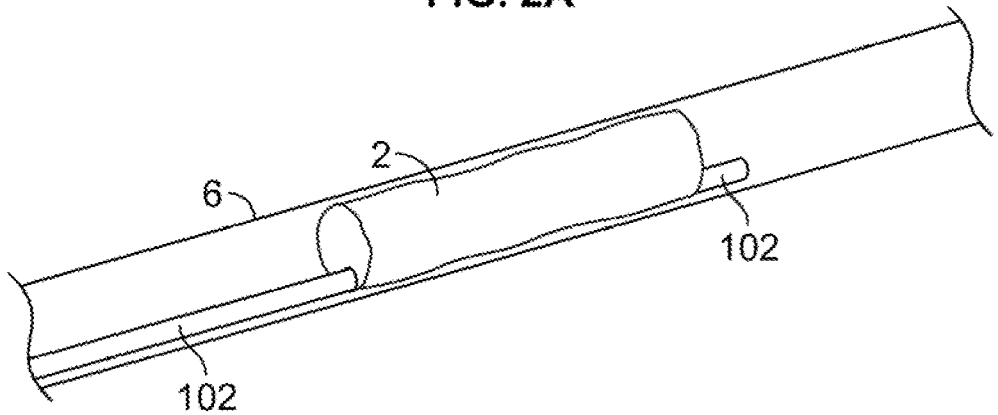
FIGS. 2B to 2F illustrate advancement of a catheter beyond an obstruction and placement of a variation of the inventive device around the obstruction.

FIG. 2B shows another variation where a microcatheter 102 traverses the obstruction 2 between the wall of the vessel 6 and the obstruction 2. As shown, the open end of the microcatheter 102 is distal to the obstruction 2 and is now positioned to deploy devices for removal of the obstruction 2. This variation shows the device after removal of any guidewire. However, some variations of the device may be placed without an accompanying guidewire. Moreover, the structures discussed herein may be directly incorporated into a guidewire assembly where deployment may require a sheath or other covering to release the components from constraint.

Figure 2C:
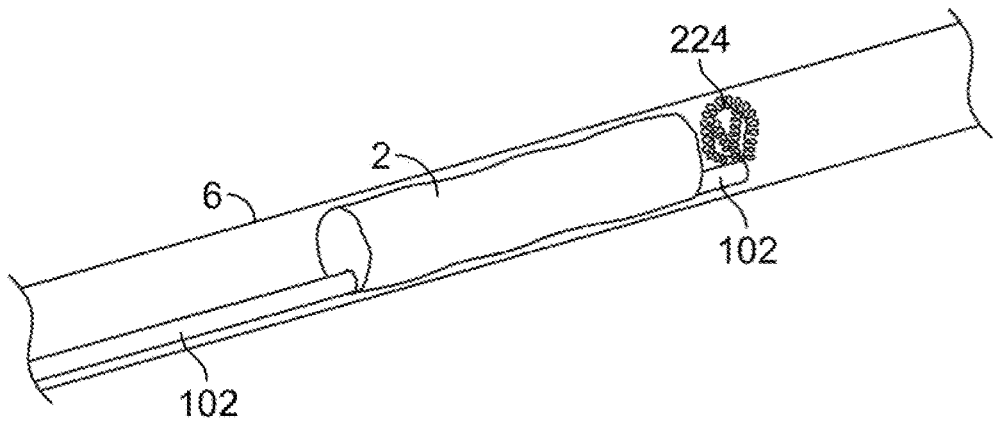

FIG. 2C illustrates deployment of a portion of the device 200 from within the microcatheter 102 distal to the obstruction 2. In this example, the third shaped section 224 deploys distally to the obstruction 2. As noted herein, depending on the properties of the device 200 as determined by the types of wires used, third shaped section 224 can be self-expanding such that it assumes, or moves towards, the expanded profile (as shown) upon deployment from the constraint of the microcatheter 102. Alternatively, the third-shaped section 224 can be actuated to assume the shape (e.g., upon reaching a transition temperature where one or more wires comprise a shape memory alloy).

Figure 2D:
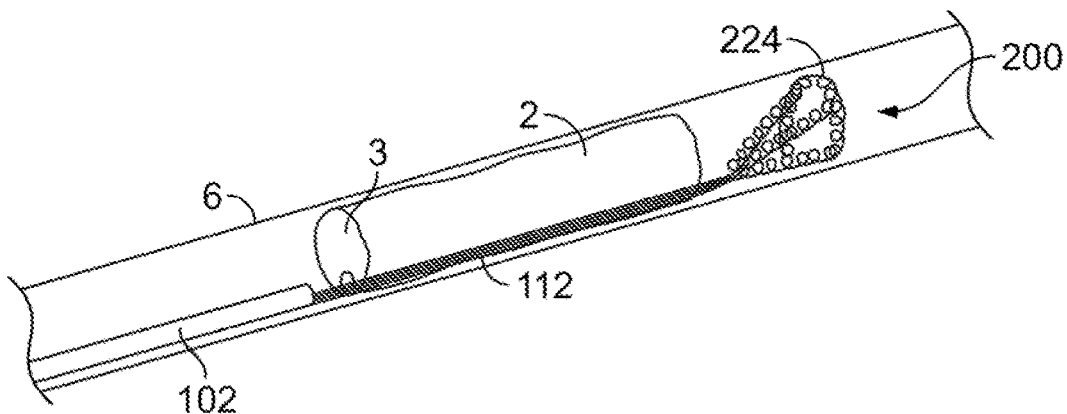

FIG. 2D shows withdrawal of the microcatheter 102 to the proximal side 3 of the obstruction 2. The spacing between the third shaped section 224 and the obstruction 2 may vary. In some cases, the third shaped section 224 will move closer towards the obstruction 2 during spacing of the remainder of the device as discussed below. The third shaped section 224 remains in place either using the inherent friction of the wires against the vessels and/or obstruction 2. Alternatively, or in combination, a wire-type member (not shown) may provide an opposing force against the third shaped section 224 as the catheter 102 moves proximal to the obstruction 2.

Figure 2E:
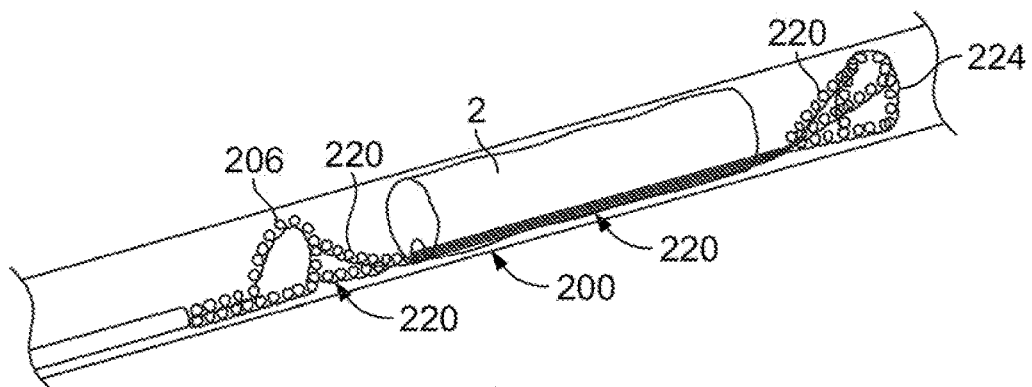

As noted above, this variation of the device 200 include a plurality of subsets 212, 214, 216, 218 that traverse between the first and third shaped sections 206, 224. As shown in FIG. 2E, eventually, second shaped section 220 spans across the obstruction 2 as shown.

Figure 2F:
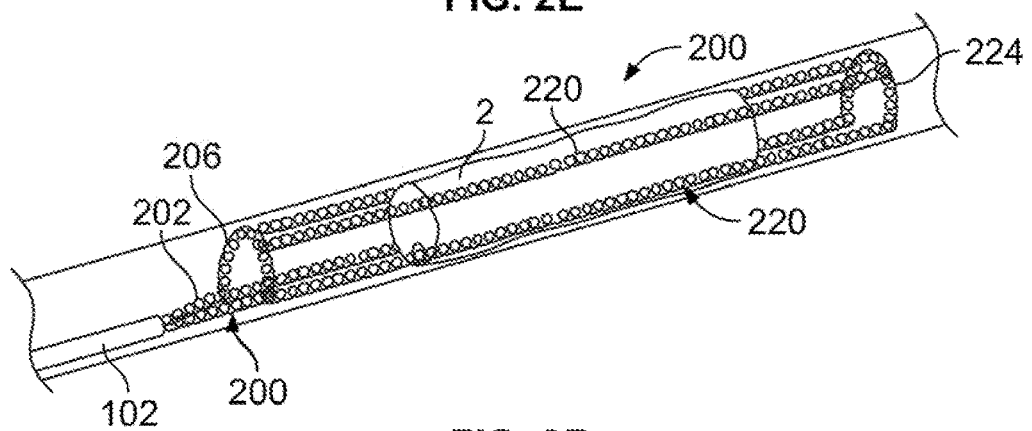

FIG. 2F illustrates the device 200 after the second shaped section 220 separate about the obstruction 2 This action causes the second shaped section 220 to span the obstruction 2 while reorienting towards an exterior of the obstruction 2. The subsets of wires may remain partially or fully within the obstruction 2. However, given that the filaments are spaced about the loops formed by the first shaped section 206 and third shaped section 224, the filaments shall separate radially over the obstruction allowing for the subsequent ensnaring and removal of the obstruction 2.

Spacing the subsets that traverse across the obstruction can occur via a number of modes such as tensioning, expanding, spreading separating and/or withdrawing the wires. Regardless of the mode used, the subsets are intended to be positioned at or near a surface of the obstruction so that they can reduce the effects of any friction between the obstruction and the lumen or vessel wall.

Figure 2G:
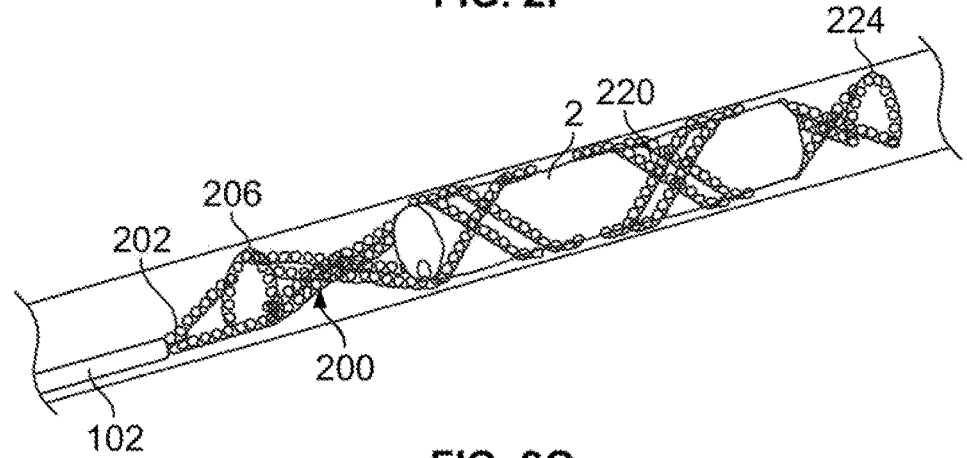
FIGS. 2G to 2H illustrate devices according to the present invention once converted to a high friction mode.
Figure 2H:
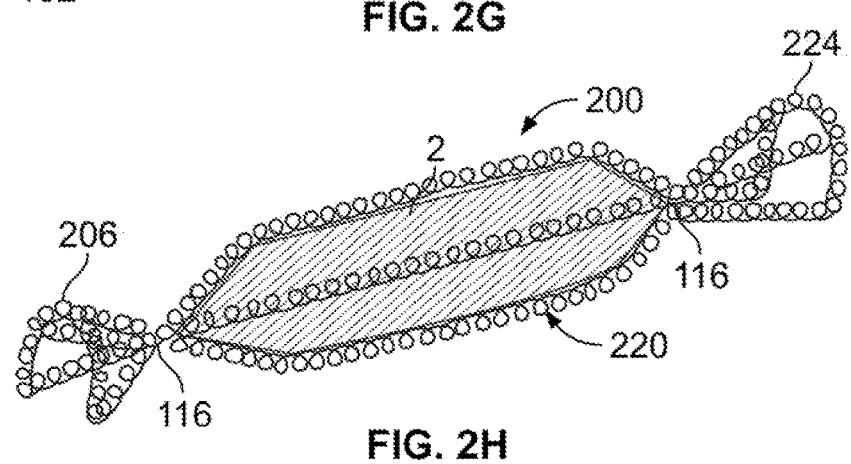

FIGS. 2G to 2H illustrates examples of the device 200 that ensnare the obstruction 2 after the device is in the configuration demonstrated by above. In these cases, the devices 200 transform from a low friction mode to a higher friction mode for removal of the obstruction 2.

FIGS. 2G to 2H illustrate rotation of the ends of the device 206 and 224 relative to one another. The resulting action converts the device 200 to a high friction mode to ensnare the obstruction 2 within the traversing section formed by the wires in the second shaped section 220. As noted herein, either connector may rotate while another connector remains stationary. Alternatively, each connector may rotate with the rate of rotation for one connector being slower than another. In yet another variation, each connector may be rotated in opposite directions.

Although the variation shows only four individual subsets of wires traversing across between the first and third shaped sections 206 and 224 any number subsets may be used so long as the rotation converts the wires into a relatively increased friction mode as compared to the low friction mode (when the subsets are in a parallel configuration). The low friction mode is represented by FIG. 2F. FIG. 2G illustrates a device in a high friction mode where the subsets of wires forming the second shaped section 220 twist and cross one another over the length of the obstruction 2. It should be noted that additional shaped sections 206, 220, and/or 224 may be required to produce the crossing pattern shown in FIG. 2G, or other preferred patterns when the device is twisted to convert to a high friction mode.

In contrast, the device 200 may be configured to transform as shown in FIG. 2H. In this case, conversion of the device 200 causes twisting at points 116 where the twist points 116 are proximal and distal to the obstruction 2. To accomplish this, the device 200 can be selected to have a length greater than the targeted obstruction 2. Upon rotation, the second shaped section 220 formed from the subsets of wires that traverse across obstruction remain uncrossed over the length of the obstruction 2. In some cases, the second shaped section 220 can experience some twisting and will not remain parallel. The relative motion of the ends 206 and 224 as well as the twist points 116 causes the second shaped section 220 to exert a compressive force on the obstruction 2 without crossing one another over the length of the obstruction. Accordingly, while the surface area in contact between the second shaped section 220 and obstruction 2 remains relatively the same, the compressive action of the second shaped section 220 onto the obstruction converts the device 200 to a high friction mode on the obstruction.

The rotation of the ends of the device 206, 224 can be performed in any number of ways as known to those skilled in the art. In either case, the obstruction 2 becomes ensnared (and/or encapsulated) and can be removed from the body.

Figure 3A:
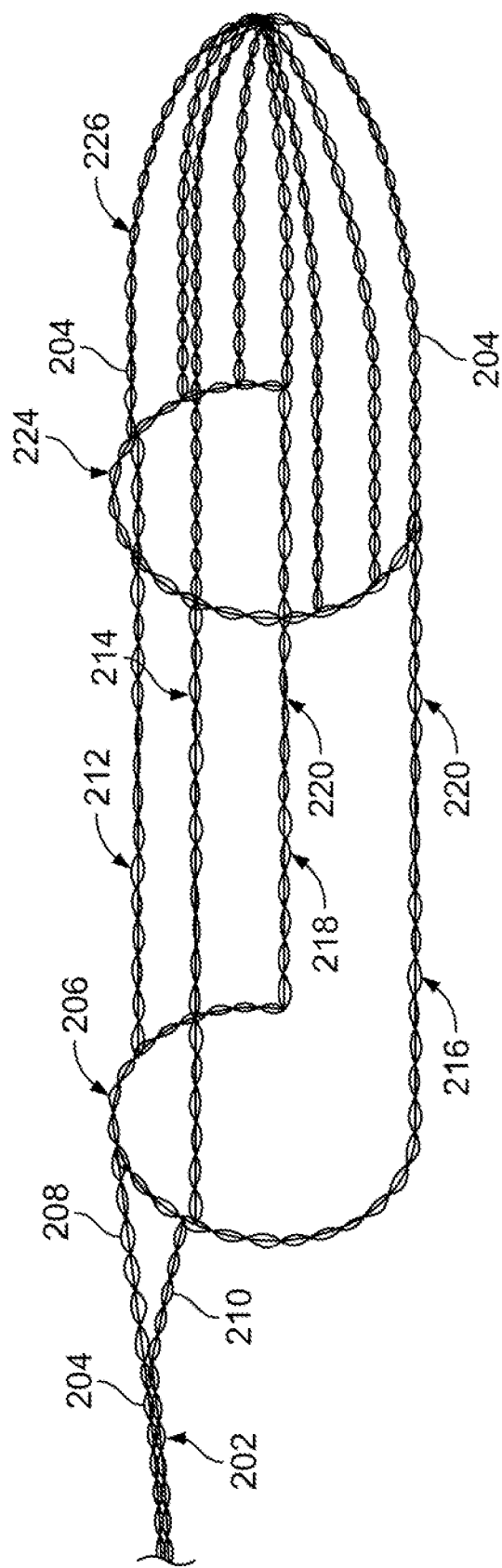
FIGS. 3A to 3B illustrate additional variations of the inventive device having a basket or mesh structure formed from diverging wires.

FIG. 3A illustrates another variation of a device where the wires 204 diverge from an end of the device 200 to form a basket 226 shape or structure. The basket structure 226 may also be referred to as a filter or surrounding portion. In variations of the device, the basket 226 is sufficiently permeable to allow blood flow therethrough. As noted above, basket 226 may be any structure that covers, encapsulates, engulfs, and/or ensnares the obstruction either fully or partially. Accordingly, although the basket 226 is illustrated as a filter/bag, the wires may diverge to form a coil, helical shape, other mesh structure, or any other structure that may translate or remove the obstruction 2 once the frictional component is addressed.

Figure 3B:
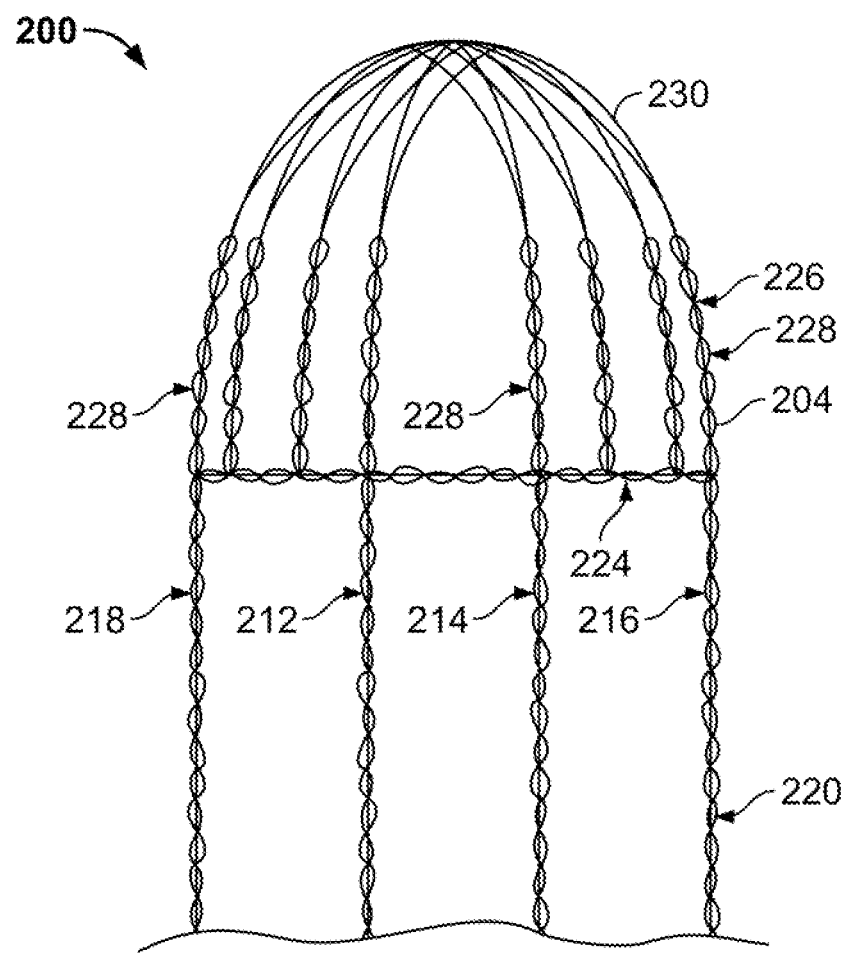

FIG. 3B shows a top view of a variation of a device 200 showing another configuration of a basket shape 226 formed by wires that diverge from an end of the device 200. In this variation, the wires 204 diverge in subsets 228 from the third shaped section 224. However, the subsets 228 continue to diverge at the far end of the device to form a mesh region 230 (i.e., an area of dense wire coverage). This mesh region 230 can increase the contact area between the wires 204 and the obstruction, which assists in removal of the obstruction. Divergence of wires could occur multiple times as wires head to the distal region of basket, creating a basket with denser and denser coverage moving distally.

Figure 3C:
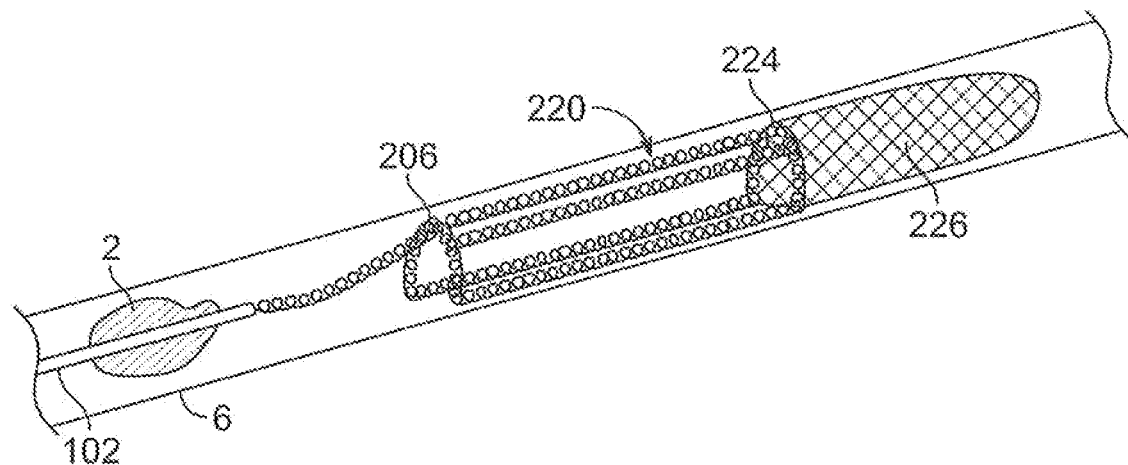
FIGS. 3C to 3D show positioning a variation of a device distally to an obstruction to ultimately translate a basket shaped section over the obstruction.

FIG. 3C depicts a variation of the device similar to that of FIG. 3A. As shown, the device 200 is deployed distally to the obstruction 2 As shown, this deployment allows the subsets of wires that extend along the device 200 to expand within the vessel 6 prior to contacting the occlusion 2.

Figure 3D:
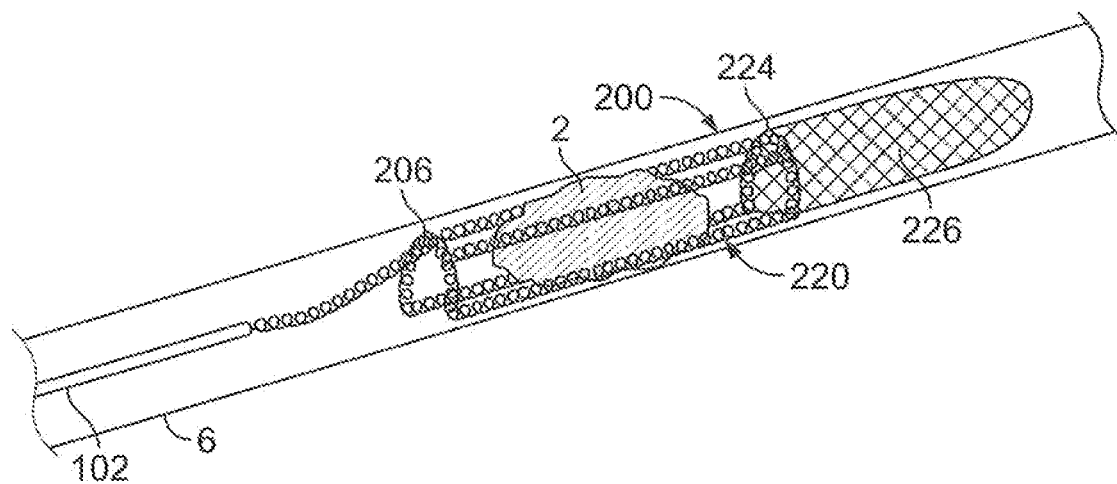

Next, as shown in FIG. 3D, the device 200 is pulled over the occlusion 2. As noted herein, the subsets of wires that form the second shaped portion 220 addresses the frictional forces that act between the obstruction and the vessel wall. Conventional devices that provide a bag attached to a wire (such as a vascular filter or distal protection device), are typically unable to remove the obstruction because they cannot overcome these frictional forces that lodge the clot against the vessel wall. Typically, such conventional devices are only designed to "catch" free floating clots. Providing low friction with respect to the clot and the vessel allows for positioning of the device without disrupting or further compacting the clot against the vessel wall. Once the wires of the device surround or are spaced about the obstruction, they reduce the friction between the clot and vessel wall by reducing points of contact. Once these wires surround the clot, they permit translation of the device to permit a basket shaped section 226 to surround the obstruction for removal. Eventually, the device 200 is pulled so that the basket shaped section 226 captures the obstruction 2 allowing it to be removed.

Figure 4A:
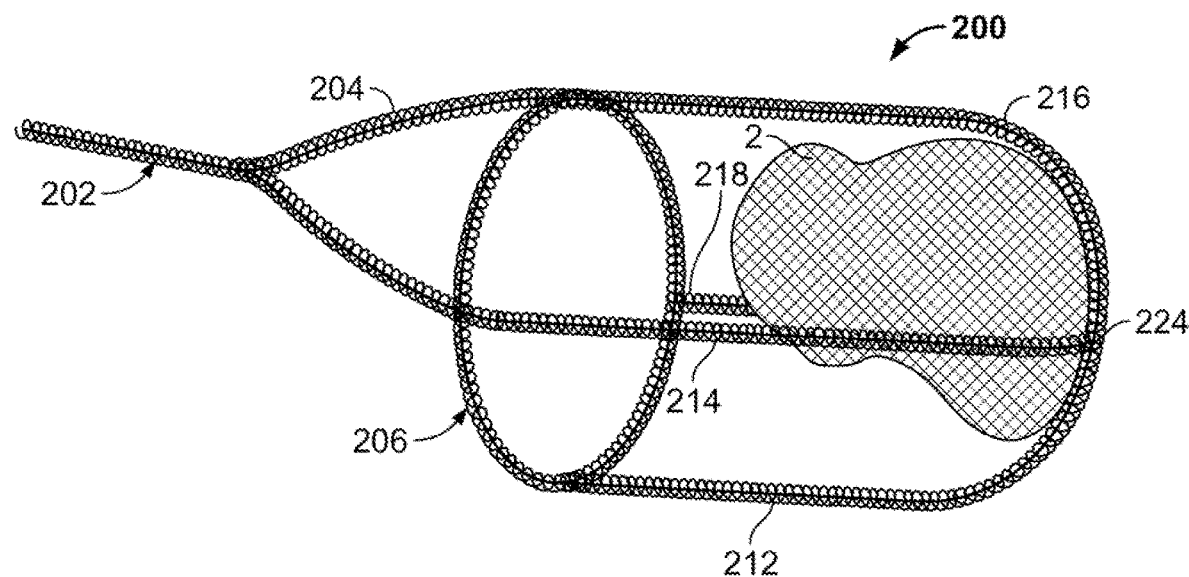
FIGS. 4A to 4B illustrate another variation of a portion a device configured to convert from a low friction mode to a high friction mode.
Figure 4B:
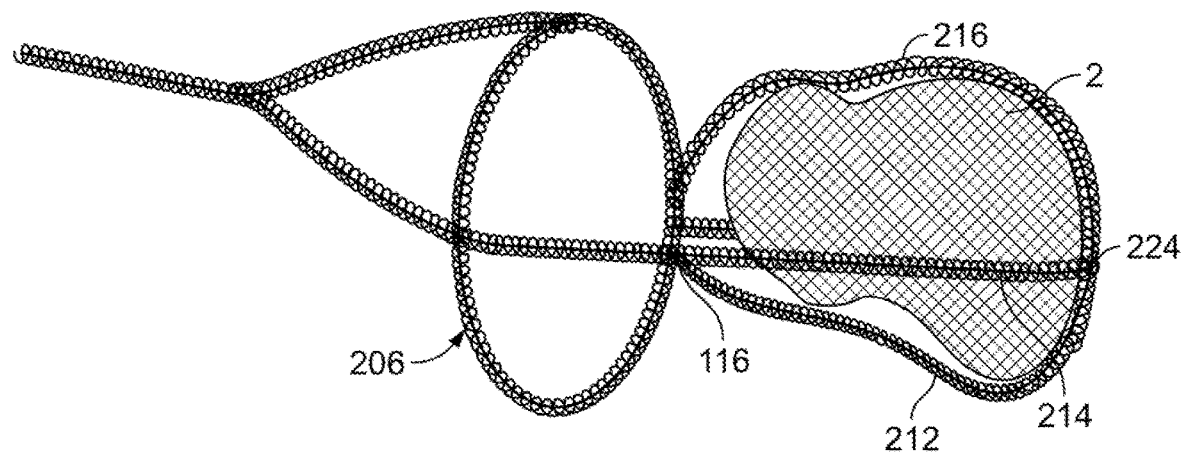

FIG. 4A illustrates a variation of a device 200 where the first shaped section is a loop shaped member 206 and the third shaped section 224 forms a closed end where the wires converge. As shown, subsets 212, 214, 216, 218 diverge from the first shaped section 206 and extend substantially parallel to the loop. Rather than converging to form another loop, the subsets converge to form a shaped section 224 having a closed end configuration. FIG. 4B illustrates the variation of FIG. 4A after it converts to a high friction mode over the obstruction 2 via rotation of the first shaped section 206. As with other variations, the number of subsets may vary as needed. In addition, the subsets of wires 212, 214, 216, 218 can further diverge to form a denser mesh pattern at or towards the third shaped section 224.

As shown, rotation of the shaped section 206 forms a twist point 116 proximal to the obstruction 2. In some cases, the subsets of wires 212, 214, 216, 218 can experience some twisting and may not remain parallel. The rotation of the shaped section 206 as well as the twist point 116 causes the subsets of wires 212, 214, 216, 218 to exert a compressive force on the obstruction 2 without crossing one another over the length of the obstruction. Accordingly, while the surface area in contact between the subsets of wires 212, 214, 216, 218 and obstruction 2 remains relatively the same, the compressive action of the subsets of wires onto the obstruction converts the device 200 to a high friction mode on the obstruction.

Figure 5:
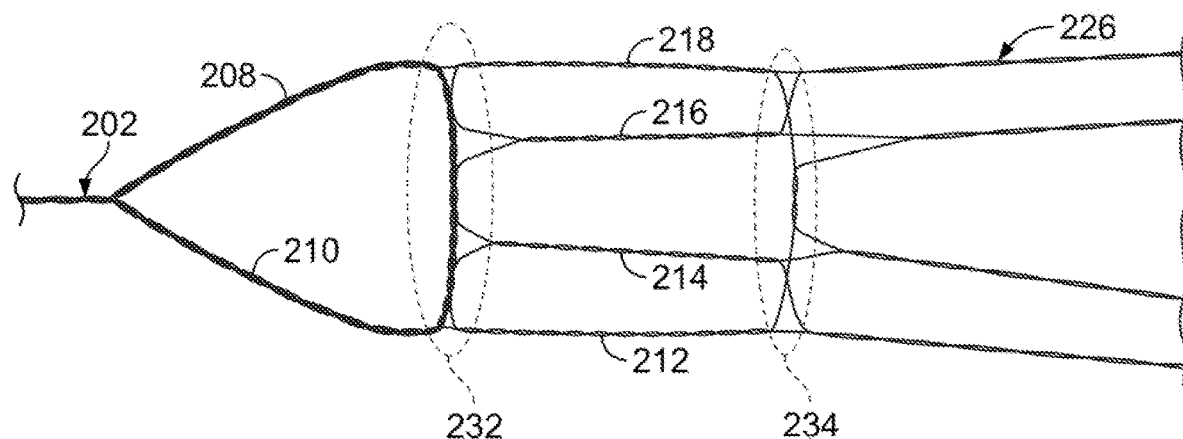
FIG. 5 illustrates an example of manufacturing a device by orienting the wires on a planar fixture.

FIG. 5 shows one example of a method for constructing devices according to the present invention. A main bundle of wires 202 is brought into a fixture (not shown). The fixture permits routing of the wires in the pattern as shown. In this particular variation, the main bundle comprises 8 wires. However, number of wires is intended for exemplary purposes only. Clearly, any number of wires may be used. As shown the wires diverge in the region marked 232 to form four separate subsets of wires 212, 214, 216, 218. Again, in this example, each subset of wire comprises 2 individual wires. This configuration is for illustrative purposes as the number of wires in each subset is not required to be the same for all.

Next, the wires converge in the region marked as 234. It is noted that if the device is constructed on a planar fixture, the wires (once oriented) will be wrapped around a cylindrical structure and heat set to impart the shapes shown above. Accordingly, the regions marked by 232 and 234 assume partial loop shapes as the planar wire assembly is wrapped around the cylindrical fixture. In alternate variations, the wires may be oriented on a cylindrical fixture and heat set into a final shape. Doing so obviously eliminates the need to wrap the planar wire assembly about a cylindrical structure.

As shown, once the wires form the region marked as 234, they diverge once again to form a basket shaped section or filter 226 as discussed above. Accordingly, upon wrapping the device wires, the region marked as 234 assumes a loop shaped section. The wires forming the basket shaped section or filter 226 can either terminate at the end of the basket or filter 226. Alternatively, the wires can be looped around such that they eventually extend back through the main bundle 202 or loop back and terminate in any portion of the device.

The above described wire form construction allows for a number of configurations depending on the particular application. For example, the individual wires 204 may themselves comprise a bundle of smaller wires or filaments. In addition, the wires can be selected from materials such as stainless steel, titanium, platinum, gold, iridium, tantalum, nitinol, and/or polymeric strands. In addition, the wires used in a device may comprise a heterogeneous structure by using combinations of wires of different materials to produce a device having the particular desired properties. For example, one or more wires in the device may comprise a shape memory or superelastic alloy to impart predetermined shapes or resiliency to the device. In some variations, the mechanical properties of select wires can be altered. In such a case, the select wires can be treated to alter properties including: brittleness, ductility, elasticity, hardness, malleability, plasticity, strength, and toughness.

In addition, the device may include a number of radiopaque wires, such as gold and platinum for improved visibility under fluoroscopic imaging. In other words, any combination of materials may be incorporated into the device. In addition to the materials, the size of the wires may vary as needed. For example, the diameters of the wires may be the same or may vary as needed.

In addition, the individual wires may have cross-sectional shapes ranging from circular, oval, d-shaped, rectangular shape, etc. Moreover, the device is not limited to having wires having the same cross-sectional shape. Instead, the device can have wires having different cross-sectional shapes. To illustrate one such example, a device can have 8-12 wires made of 0.003" round superelastic material (e.g., nitinol). The device may additionally have 2-4 wires made from 0.002" platinum for fluoroscopy. Of the 8-12 nitinol wires, 1-4 of these wires can be made of a larger diameter or different cross-section to increase the overall strength of the device. Finally, a couple of polymer fibers can be added where the fibers have a desired surface property for clot adherence, etc. Such a combination of wires provides a composite device with properties not conventionally possible in view of other formation means (such as laser cutting or etching the shape from a tube or joining materials with welds, etc.). Clearly, any number of permutations is possible given the principles of the invention.

In another example, the device may be fabricated from wires formed from a polymeric material or composite blend of polymeric materials. The polymeric composite can be selected such that it is very floppy until it is exposed to either the body fluids and or some other delivered activator that causes the polymer to further polymerize or stiffen for strength. Various coatings could protect the polymer from further polymerizing before the device is properly placed. The coatings could provide a specific duration for placement (e.g., 5 minutes) after which the covering degrades or is activated with an agent (that doesn't affect the surrounding tissues) allowing the device to increase in stiffness so that it doesn't stretch as the thrombus is pulled out. For example, shape memory polymers would allow the device to increase in stiffness.

As discussed herein, the shaped section connectors may be other structures than loops. Moreover, variations of the invention include connectors that may be drawn down to a smaller size to facilitate removal from the body after securing the obstruction. This may be accomplished by torquing the device or part thereof, by re-sheathing part or all of the device or by any mechanical means designed into the features of the device itself. Any of these actions, or combination thereof, may also serve to compress or decrease the diameter of the obstruction itself to facilitate removal from the body.

As with the above examples, the illustrated variation shown above, the shaped portions are formed in a loop or partial loop shape. However, as described herein, the connectors may also comprise various alternate shapes (e.g., a circle, an arcuate shape, a partial circular shape, a loop, an oval, a square, a rectangle, a polygon, an overlapping loop, a pair of semi-circles, a flower shape, and a FIG. 8, other shapes, etc.) FIGS. 6A to 6D illustrate some possible shapes for use in the device. The various shapes may be heat set to be either self expanding (i.e., superelastic) or the use of shape memory alloys can allow for the device to assume the particular shape upon reaching a desired transition temperature. In certain cases, such as where the shape is an overlapping loop, a pair of semi-circles, a flower shape, a FIG. 8, or other complex/discontinuous shape, such a shape may be formed by a single bundle or by one or more separate portions of wire that diverge from the main bundle.

Figure 6A:
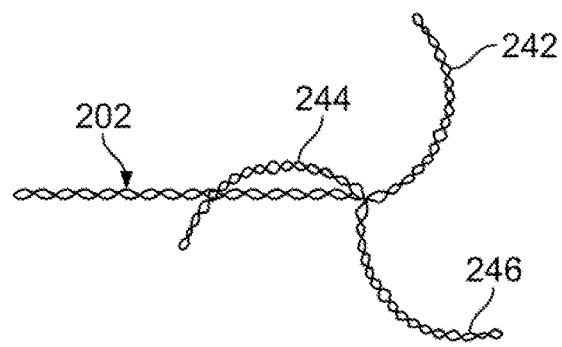
FIGS. 6A to 6D illustrate variations of the shaped sections that can be formed from the wires forming the device.

FIG. 6A illustrates a main bundle of wires 202 that diverge in three arcuate shaped portions 242, 244, 246. Naturally, the device may have more or less arcuate shaped sections. In this illustration, the segments forming the arcuate 242, 244, 246 shaped portions may simply bend to form segments that traverse across the device (as shown above.) However, such traversing sections are omitted to illustrate the arcuate shape.

Figure 6B:
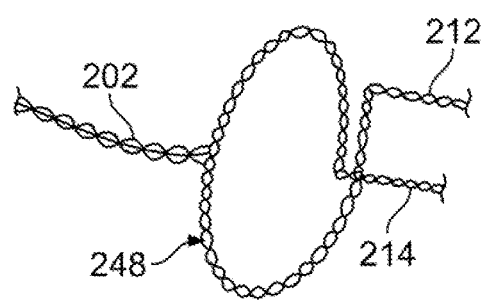

FIG. 6B illustrates a main bundle 202 that ultimately diverges to form an overlapping loop shape 248. As shown, the ends of the overlapping loop may then proceed to form the traversing subsets 212, 214 discussed above. In addition, additional subsets of wires may diverge from a location other than the end of the overlapping loop shape 248.

Figure 6C:
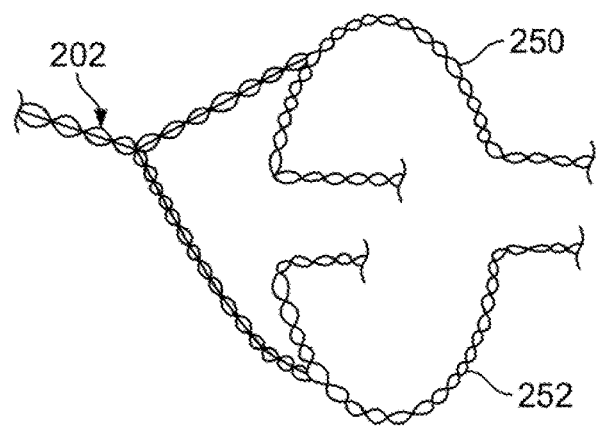

FIG. 6C illustrates a main bundle that diverges to form two semi-circular or partial circular shapes 250, 252. In this variation, the two shapes are located along the same axial section of the device but the shapes are separate. Again, the ends of the partial circular shapes 250, 252 may diverge to form the traversing section of the device. Alternatively, the traversing wires can come from other locations.

Figure 6D:
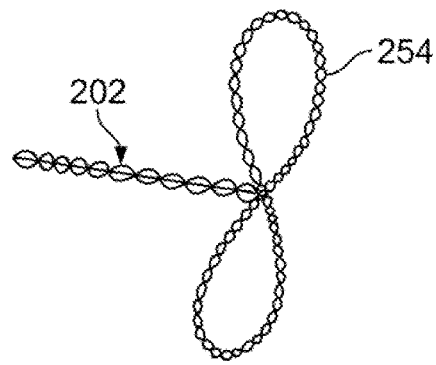

FIG. 6D illustrates a main bundle 202 that diverges to form a "figure-8" shape. As with other variations, additional subsets (not shown) of wires may diverge from the "figure-8" shape to form the traversing subsets. In addition, flower shaped sections may be formed by the use of additional circular shapes that form the petals of the flower shape or via the use of multiple "figure-8" shapes.

The exemplary shapes discussed above permit the shaped section to adjust in diameter in response to placement in varying diameters of body lumens. It is noted that a device may have different shaped sections on different ends of the device.

While many different shapes are contemplated to be within the scope of this disclosure, the shapes will depend upon the ultimate application of the device. As noted herein, the illustrated examples have particular applicability in retrieving obstructions from the vasculature. Accordingly, for these applications the shaped sections should form a shape so that they can expand against a vessel wall without causing trauma to the vessel. For example, upon release from the catheter, the shaped section can assume their resting shape and expand within the vessel. The resting shape can be constructed to have a size slightly greater than that of the vessel. Sizing the device relative to the target vessel may assist in placing the parts of the device against a vessel.

In an additional aspect, the shaped sections may be designed to have an unconstrained shape that is larger than the intended target vessel or simply different than a cross sectional profile of the intended vessel (i.e., not circular or tubular, but e.g., linear or other different shape). In such an example, as the shaped section is released from the delivery catheter, the shape section attempts to return to the unconstrained shape. In those variations where the unconstrained shape is different from the circular profile of the vessel, the leading wire assumes a shape that accommodates the vessel but is more rigid and stable since its unconstrained shape is entirely different from that of the vessel. In other words, the shaped section continually exerts an outward force on the vessel.

In yet another aspect, the shaped sections shown herein may not necessarily lie in the same plane. Instead, they can be axially spaced by an offset. One benefit of constructing the device to have non-planar shaped section is that the configuration might allow for delivery of the device delivered via a smaller microcatheter because the shaped sections do not interfere with one another when collapsed to fit within the microcatheter.

Another aspect applicable to all variations of the devices is to configure the devices (whether the traversing filament or the surrounding portion) for better adherence to the obstruction. One such mode includes the use of coatings that bond to certain clots (or other materials causing the obstruction.) For example, the wires may be coated with a hydrogel or adhesive that bonds to a thrombus. Accordingly, as the device secures about a clot, the combination of the additive and the mechanical structure of the device may improve the effectiveness of the device in removing the obstruction.

Figure 6E:
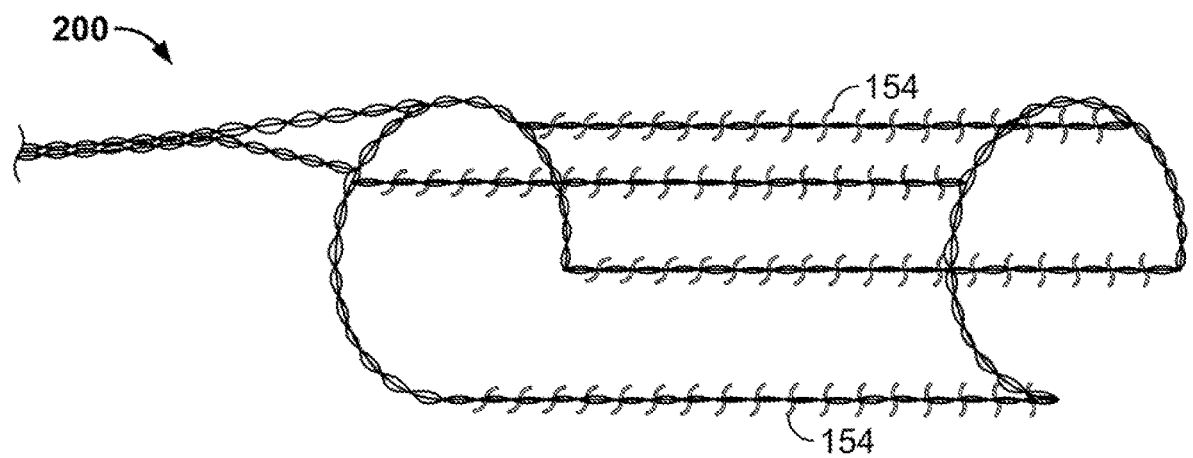
FIG. 6E illustrates hooks, fibers, and/or barbs for increasing the ability of the device to remove obstructions.

Such improvements may also be mechanical or structural. For example, as shown in FIG. 6E, the traversing members may have hooks, fibers, or barbs 154 that grip into the obstruction when the device converts to a high friction mode. The hooks, fibers, or barbs 154 incorporated into any portion of the device. However, it will be important that such features do not hinder the ability of the practitioner to remove the device from the body.

In addition to additives, the device can be coupled to an RF or other power source (such as 14 or 16 in FIG. 1), to allow current, ultrasound or RF energy to transmit through the device and induce clotting or cause additional coagulation of a clot or other the obstruction.

The methods described herein may also include treating the obstruction prior to attempting to remove the obstruction. Such a treatment can include applying a chemical or pharmaceutical agent with the goal of making the occlusion shrink or to make it more rigid for easier removal. Such agents include, but are not limited to chemotherapy drugs, or solutions, a mild formalin, or aldehyde solution.

Although not illustrated, the devices and methods described herein may also be useful in removing obstructions lodged within bifurcations in the anatomy. Generally, bifurcations greatly increase the frictional forces on the obstructions since the obstruction tends to be lodged in both branching sections of the bifurcation. In such cases, the use of the presently described devices and methods may also include an additional "puller" device that advances beyond the portion of the obstruction partially located in the bifurcated vessel.

As for other details of the present invention, materials and manufacturing techniques may be employed as within the level of those with skill in the relevant art. The same may hold true with respect to method-based aspects of the invention in terms of additional acts that are commonly or logically employed. In addition, though the invention has been described in reference to several examples, optionally incorporating various features, the invention is not to be limited to that which is described or indicated as contemplated with respect to each variation of the invention.

Figure 7A:
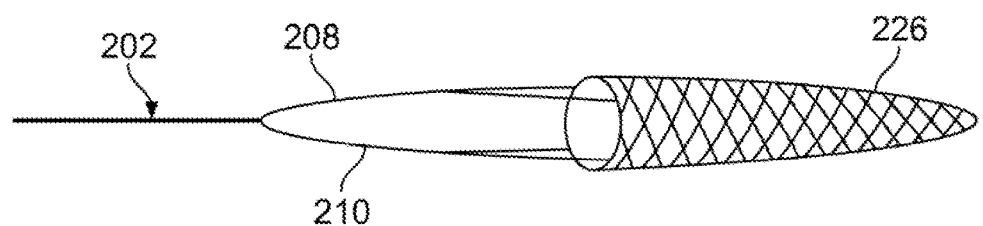
FIGS. 7A to 7C illustrate additional variations of shapes for use in the devices according to the present invention.
Figure 7B:
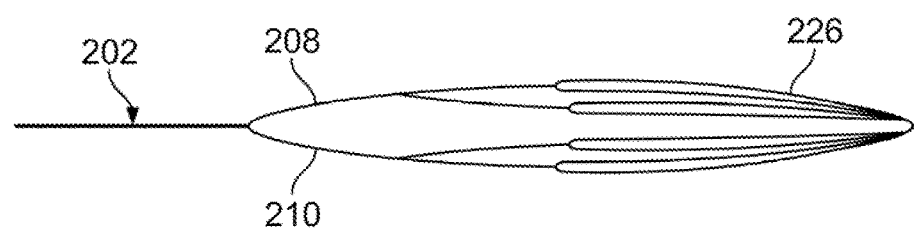
Figure 7C:
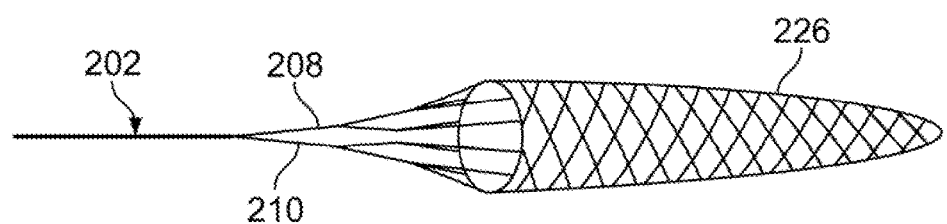
Figure 8A:
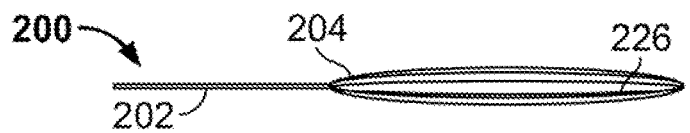
FIGS. 8A to 8F also illustrate additional variations of obstruction removal devices, focusing mainly on variations of the surrounding portion.
Figure 8B:
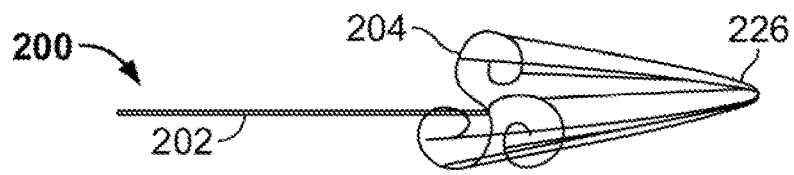
Figure 8C:
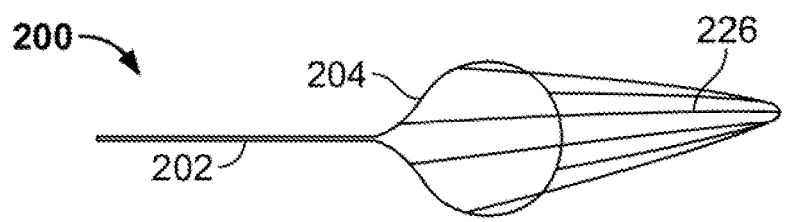
Figure 8D:
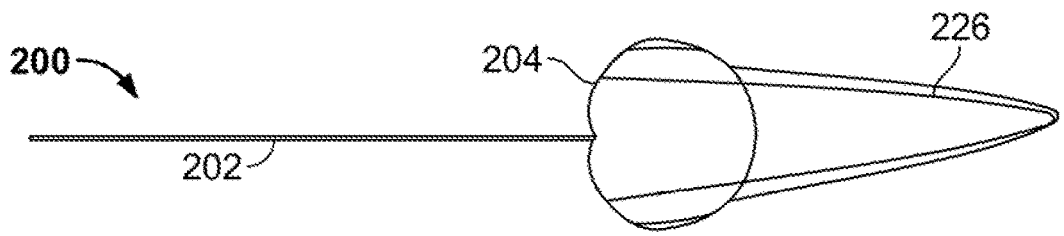
Figure 8E:
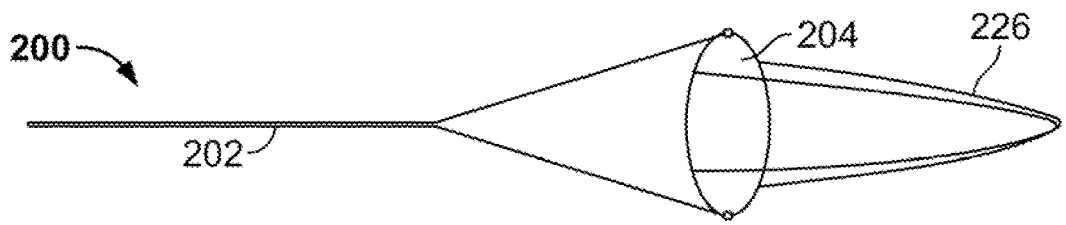
Figure 8F:
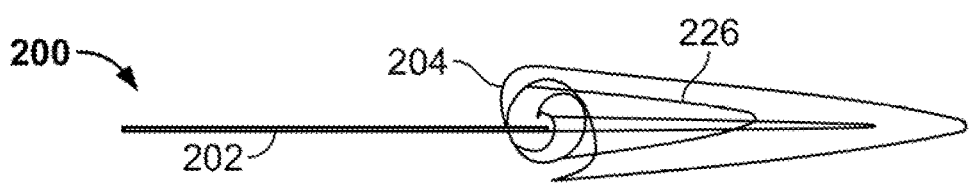

FIGS. 7A to 7C illustrate additional variations of obstruction removal devices. In these variations, the wires may diverge from the main wire bundle 202 to form any number of shapes and structures and specifically not form loop or the shaped sections discussed above. For example, in FIGS. 7A to 7B the wires diverge to ultimately form a basket or filter shape 226.

FIGS. 8A to 8F illustrate various additional configurations for construction of join-less devices 200. As shown, the main bundle of wires 202 diverges so that one or more wires forms the illustrated shapes.

Figure 9A:
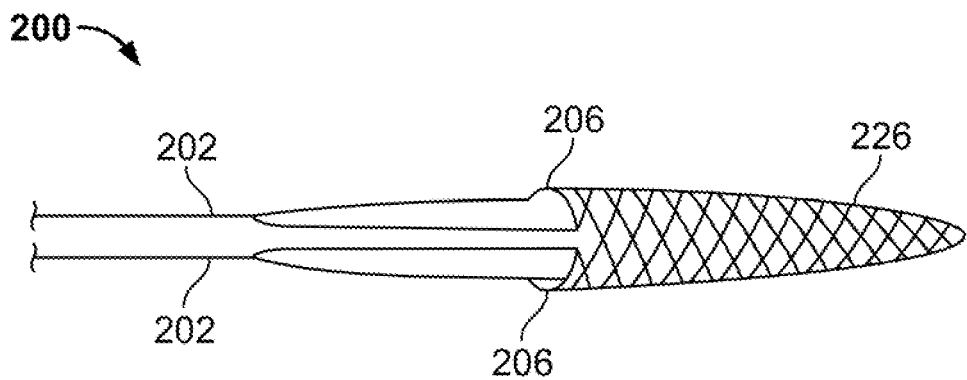
FIGS. 9A to 9C show another variation of a medical device having multiple bundles of wires where the wires diverge to form capturing sections.
Figure 9B:
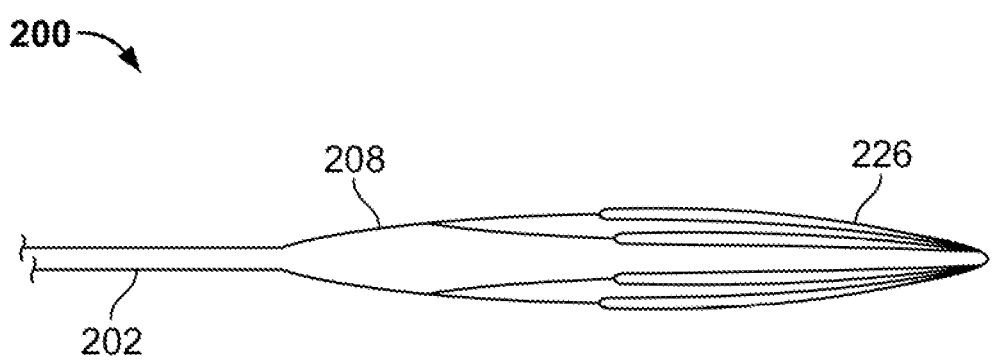
Figure 9C:
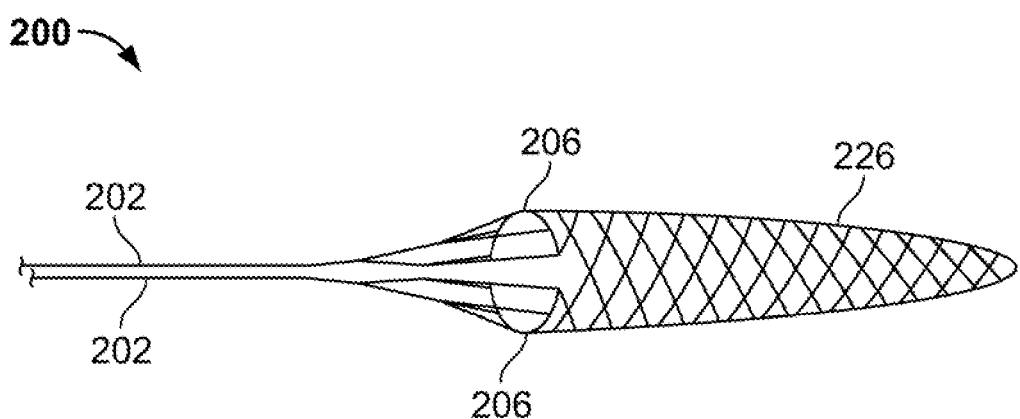

FIGS. 9A to 9C show another variation of a medical device according to the principles of the invention. As shown, the device 200 comprises a first and second main bundles 202, where the main bundles comprise a plurality of wires. The devices further include a first shape and second shapes 206 formed by a divergence of the plurality of wires into a plurality of individual first subsets of wires. In these variations, the wires diverge to form a network of individual single wires as shown in region 226. The shapes form a three dimensional structure that is useful for removal of obstruction from within the body. In FIG. 9B, each shape comprises a structure that forms a portion of the basket where a network of wires forms an end of the basket. In FIGS. 9A and 9C the network of wires forms the entire basket.

As noted above, the shapes 206 may range from a circle, an arcuate shape, a partial circular shape, a loop, an oval, a square, a rectangle, a polygon, an overlapping loop, a pair of semi-circles, a flower shape, and a FIG. 8 (as shown above).

Various changes may be made to the invention described and equivalents (whether recited herein or not included for the sake of some brevity) may be substituted without departing from the true spirit and scope of the invention. Also, any optional feature of the inventive variations may be set forth and claimed independently, or in combination with any one or more of the features described herein. Accordingly, the invention contemplates combinations of various aspects of the embodiments or combinations of the embodiments themselves, where possible. Reference to a singular item, includes the possibility that there are plural of the same items present. More specifically, as used herein and in the appended claims, the singular forms "a," "and," "said," and "the" include plural references unless the context clearly dictates otherwise.

I claim:

1. A method of improving blood flow in a blood vessel having an obstruction, the method comprising:
   advancing a catheter into the blood vessel, the catheter containing an obstruction removal device having an expandable mesh structure extending between a near end and a far end and comprising a continuous construction of a metal alloy, having a plurality of interconnected segments, wherein the expandable mesh structure includes an intermediate portion between first and second regions of the structure in which the mesh structure converges inwardly, and wherein at least one of the plurality of segments of the mesh structure along the intermediate portion extends longitudinally and substantially parallel to another of the segments of the mesh structure;
   deploying the far end and the near end of the mesh structure respectively beyond a distal end and a proximal end of the obstruction such that the mesh structure spans across the obstruction and the intermediate portion expands within the vessel to embed into the obstruction;
   holding the obstruction via the intermediate portion of the mesh structure between the first and second regions of the structure in which the mesh structure converges inwardly; and
   withdrawing the obstruction removal device and obstruction from the vessel to improve blood flow in the blood vessel.

2. The method of claim 1, where the intermediate portion forms a shaped section about the obstruction between the first and second regions.

3. The method of claim 1, where deploying the far end of the obstruction removal device beyond the distal end of the obstruction comprises withdrawing the catheter relative to the obstruction removal device such that the far end of the obstruction removal device remains distal to the obstruction.

4. The method of claim 1, where the intermediate portion comprises at least one filament.

5. The method of claim 1, where the mesh structure of the obstruction removal device is self-expanding.

6. The method of claim 1, where allowing the intermediate portion to embed into the obstruction comprises allowing the intermediate portion to embed into the obstruction without substantially dislocating or mobilizing the obstruction within the blood vessel.

7. The method of claim 1, where the obstruction removal device is fabricated from a process selected from the group consisting of a photochemical etching, mechanical drilling, weaving, braiding, and laser cutting.

8. The method of claim 1, further comprising advancing a catheter adjacent to the obstruction and where advancing the obstruction removal device comprises advancing the obstruction removal device and catheter through the catheter to the obstruction.

9. The method of claim 8, further comprising withdrawing at least a portion of the obstruction removal device within the catheter and removing the catheter from the vessel.

10. The method of claim 1, where the obstruction comprises a blood clot, plaque, cholesterol, thrombus, a naturally occurring foreign body, a non-naturally occurring foreign body or a combination thereof.

11. The method of claim 1, where the first region is located distal of a proximal end of the mesh structure, and proximal of a distal end of the mesh structure.

12. The method of claim 11, where the second region is located distal of a proximal end of the mesh structure, and proximal of a distal end of the mesh structure.

13. The method of claim 12, where the second region is located distal of the first region.

14. A method of improving blood flow in a blood vessel having an obstruction, the method comprising:
   advancing an obstruction removal device within the blood vessel where the obstruction removal device comprises a mesh structure extending between a near end and a far end, where the mesh structure comprises a continuous wire construction with a plurality of wires, wherein the mesh structure includes an intermediate portion between first and second regions of the structure in which the wires converge inwardly, and wherein at least one of the wires along the intermediate portion extends longitudinally and substantially parallel to another one of the wires;
   deploying the far end and the near end of the mesh structure such that the mesh structure spans across the obstruction and the intermediate portion expands within the vessel to embed into the obstruction;
   holding the obstruction via the intermediate portion of the mesh structure between the first and second regions of the structure in which the mesh structure converges inwardly; and
   withdrawing the obstruction removal device and obstruction from the vessel to improve blood flow in the blood vessel.

15. The method of claim 14, where the intermediate portion forms a shaped section about the obstruction between the first and second regions.

16. The method of claim 14, where deploying the obstruction removal device comprises advancing a catheter through the obstruction.

17. The method of claim 14, where the mesh structure of the obstruction removal device is self-expanding.

18. The method of claim 14, where allowing the intermediate portion to embed into the obstruction comprises allowing the intermediate portion to embed into the obstruction without substantially dislocating or mobilizing the obstruction within the blood vessel.

19. The method of claim 14, where the first region is located distal of a proximal end of the mesh structure, and proximal of a distal end of the mesh structure.

20. The method of claim 19, where the second region is located distal of a proximal end of the mesh structure, and proximal of a distal end of the mesh structure.

21. The method of claim 20, where the second region is located distal of the first region.

* * * * *